(12) United States Patent
Chang

(10) Patent No.: US 6,987,118 B2
(45) Date of Patent: Jan. 17, 2006

(54) TETRAHYDROISOQUINOLINE DERIVATIVES AS PPAR-ALPHA ACTIVATORS

(75) Inventor: George Chang, Old Saybrook, CT (US)

(73) Assignee: Pfizer Inc., New York, NY (US)

(*) Notice: Subject to any disclaimer, the term of this patent is extended or adjusted under 35 U.S.C. 154(b) by 0 days.

(21) Appl. No.: 10/839,671

(22) Filed: May 5, 2004

(65) Prior Publication Data

US 2004/0248934 A1     Dec. 9, 2004

Related U.S. Application Data

(60) Provisional application No. 60/472,568, filed on May 21, 2003.

(51) Int. Cl.
  *C07D 401/12*   (2006.01)
  *A61K 31/47*    (2006.01)
(52) U.S. Cl. ........................ 514/307; 546/146
(58) Field of Classification Search ............ 514/307; 546/146
  See application file for complete search history.

(56) References Cited

U.S. PATENT DOCUMENTS 5,658,944 A    8/1997   Chapman, Jr. et al. ..... 514/478

FOREIGN PATENT DOCUMENTS

| | | |
|---|---|---|
| CA | 2448639 | 12/2002 |
| EP | 1452521 | 9/2004 |
| WO | WO 9736579 | 10/1997 |
| WO | WO 9805331 | 2/1998 |
| WO | WO 0023407 | 4/2000 |
| WO | WO 0100603 | 1/2001 |
| WO | WO 0117994 | 3/2001 |
| WO | WO 0140207 | 6/2001 |
| WO | WO 9210468 | 2/2002 |
| WO | WO 0250047 | 6/2002 |
| WO | WO 02062774 | 8/2002 |
| WO | WO 02064139 | 8/2002 |
| WO | WO 02064549 | 8/2002 |
| WO | WO 02096904 | 12/2002 |
| WO | WO 03016265 | 2/2003 |
| WO | WO 03072102 | 9/2003 |

OTHER PUBLICATIONS

English language equivalent of WO 02/096904, Dec. 2002.
English language equivalent of WO 03/016265, Feb. 2003.

*Primary Examiner*—Zinna Northington Davis
(74) *Attorney, Agent, or Firm*—Gregg C. Benson; Lisa A. Samuels

(57) ABSTRACT

PPAR alpha activators, pharmaceutical compositions containing such compounds and the use of such compounds to elevate certain plasma lipid levels, including high density lipoprotein-cholesterol and to lower certain other plasma lipid levels, such as LDL-cholesterol and triglycerides and accordingly to treat diseases which are exacerbated by low levels of HDL cholesterol and/or high levels of LDL-cholesterol and triglycerides, such as atherosclerosis and cardiovascular diseases, in mammals, including humans.

6 Claims, No Drawings

TETRAHYDROISOQUINOLINE DERIVATIVES AS PPAR-ALPHA ACTIVATORS

CROSS-REFERENCE TO RELATED APPLICATION

This application claims the benefit of U.S. Provisional application No. 60/472,568, filed May 21, 2003, which is incorporated herein by reference for all purposes.

BACKGROUND OF INVENTION

The present invention relates to peroxisome proliferator activator receptor (PPAR) agonists, in particular, PPARα agonists, pharmaceutical compositions containing such agonists and the use of such agonists to treat atherosclerosis, hypercholesterolemia, hypertriglyceridemia, diabetes, obesity, osteoporosis and Syndrome X (also known as metabolic syndrome) in mammals, including humans.

Atherosclerosis, a disease of the arteries, is recognized to be the leading cause of death in the United States and Western Europe. The pathological sequence leading to atherosclerosis and occlusive heart disease is well known. The earliest stage in this sequence is the formation of "fatty streaks" in the carotid, coronary and cerebral arteries and in the aorta. These lesions are yellow in color due to the presence of lipid deposits found principally within smooth-muscle cells and in macrophages of the intima layer of the arteries and aorta. Further, it is postulated that most of the cholesterol found within the fatty streaks, in turn, gives rise to development of the "fibrous plaque," which consists of accumulated intimal smooth muscle cells laden with lipid and surrounded by extra-cellular lipid, collagen, elastin and proteoglycans. These cells plus matrix form a fibrous cap that covers a deeper deposit of cell debris and more extra-cellular lipid. The lipid is primarily free and esterified cholesterol. The fibrous plaque forms slowly, and is likely in time to become calcified and necrotic, advancing to the "complicated lesion," which accounts for the arterial occlusion and tendency toward mural thrombosis and arterial muscle spasm that characterize advanced atherosclerosis.

Epidemiological evidence has firmly established hyperlipidemia as a primary risk factor in causing cardiovascular disease (CVD) due to atherosclerosis. In recent years, leaders of the medical profession have placed renewed emphasis on lowering plasma cholesterol levels, and low density lipoprotein cholesterol in particular, as an essential step in prevention of CVD. The upper limits of "normal" are now known to be significantly lower than heretofore appreciated. As a result, large segments of Western populations are now realized to be at particularly high risk. Additional independent risk factors include glucose intolerance, left ventricular hypertrophy, hypertension, and being of the male sex. Cardiovascular disease is especially prevalent among diabetic subjects, at least in part because of the existence of multiple independent risk factors in this population. Successful treatment of hyperlipidemia in the general population, and in diabetic subjects in particular, is therefore of exceptional medical importance.

In spite of the early discovery of insulin and its subsequent widespread use in the treatment of diabetes, and the later discovery of and use of sulfonylureas, biguanides and thiazolidenediones, such as troglitazone, rosiglitazone or pioglitazone, as oral hypoglycemic agents, the treatment of diabetes could be improved. The use of insulin typically requires multiple daily doses. Determination of the proper dosage of insulin requires frequent estimations of the sugar in urine or blood. The administration of an excess dose of insulin causes hypoglycemia, with effects ranging from mild abnormalities in blood glucose to coma, or even death. Treatment of non-insulin dependent diabetes mellitus (Type II diabetes, NIDDM) usually consists of a combination of diet, exercise, oral hypoglycemic agents, e.g., thiazolidenediones, and in more severe cases, insulin. However, the clinically available hypoglycemic agents can have side effects that limit their use. In the case of insulin dependent diabetes mellitus (Type I), insulin is usually the primary course of therapy.

U.S. Pat. No. 5,658,944, WO92/10468, WO97/36579, WO98/05331 and WO 00/23407 disclose agents for the treatment of atherosclerosis, obesity and diabetes.

International Publication Nos. WO 02/064549 and 02/064139 disclose certain compounds which are PPARα activators.

International Publication No. WO 01/40207 discloses certain substituted oxazoles and thiazoles derivatives as hPPAR alpha activators. International Publication No. WO 01/17994 discloses certain oxazole PPAR antagonists. WO 01/00603 discloses certain thiazole and oxazole derivatives and their pharmaceutical use. WO 02/46174 discloses certain 1,2,4-oxadiazole derivatives as hPPAR alpha agonists. International Publication No. WO 02/062774 discloses certain thiazole derivatives for treating PPAR related disorders.

International Publication No. WO 02/096904 discloses certain novel heterocyclic derivatives and medicinal use thereof.

Provisional application Ser. No. 60/429,506, filed Nov. 26, 2002, discloses certain PPAR activators, including piperidine-containing compounds.

Thus, although there are a variety of anti-atherosclerosis and diabetes therapies, there is a continuing need and a continuing search in this field of art for alternative therapies.

SUMMARY OF THE INVENTION

The present invention provides compounds of formula I

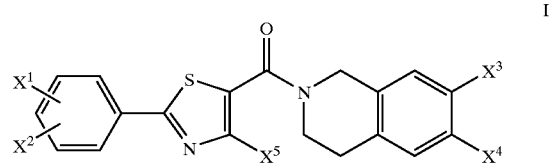

a prodrug of said compound or a pharmaceutically acceptable salt of said compound or prodrug; wherein $X^1$ and $X^2$ are each independently a) hydrogen, b) halo, c) $(C_1-C_4)$alkyl optionally substituted with one to three fluoro or d) $(C_1-C_4)$alkoxy optionally substituted with one to three fluoro;

one of $X^3$ and $X^4$ is hydrogen and the other is —Y—C$(R^1)(R^2)$—COOH;

Y is —O— or —S—;

$R^1$ and $R^2$ are each independently a) hydrogen or b) $(C_1-C_4)$alkyl;

$X^5$ is —CH$_3$ or —CF$_3$.

More particularly, the present invention provides compounds of formula I wherein $X^1$ and $X^2$ are each independently a) hydrogen, b) —CF$_3$, c) —OCF$_3$, d) $(C_1-C_4)$alkyl, e) —OCH$_3$ or f) halo;

$X^3$ is —Y—C$(R^1)(R^2)$—COOH and $X^4$ is hydrogen;

Y is —O—;
X⁵ is —CH₃.
Even more particularly, the present invention provides such compounds of formula I wherein
one of $X^1$ and $X^2$ is hydrogen and the other is —CF₃;
$R^1$ and $R^2$ are each methyl.
Even more particularly, the present invention provides such compounds of formula I wherein
one of $X^1$ and $X^2$ is hydrogen and the other is —OCF₃;
$R^1$ and $R^2$ are each methyl.
Even more particularly, the present invention provides such compounds of formula I wherein
$X^1$ and $X^2$ are each hydrogen;
$R^1$ and $R^2$ are each methyl.
Even more particularly, the present invention provides such compounds of formula I wherein
one of $X^1$ and $X^2$ is hydrogen and the other is t-butyl;
$R^1$ and $R^2$ are each methyl.
Even more particularly, the present invention provides such compounds of formula I wherein
one of $X^1$ and $X^2$ is hydrogen and the other is —OCH₃;
$R^1$ and $R^2$ are each methyl.
Even more particularly, the present invention provides such compounds of formula I wherein
$X^1$ and $X^2$ are each —CF₃;
$R^1$ and $R^2$ are each methyl.
Even more particularly, the present invention provides such compounds of formula I wherein
$X^1$ and $X^2$ are each —OCH₃;
$R^1$ and $R^2$ are each methyl.
Even more particularly, the present invention provides such compounds of formula I wherein
one of $X^1$ and $X^2$ is hydrogen and the other is halo;
$R^1$ and $R^2$ are each methyl.
In another aspect, the present invention more particularly provides compounds of formula I wherein
$X^1$ and $X^2$ are each independently a) hydrogen, b) —CF₃, c) —OCF₃, d) (C₁–C₄)alkyl, e) —OCH₃ or f) halo;
$X^3$ is hydrogen and $X^4$ is —Y—C(R¹)(R²)—COOH;
Y is —O—;
X⁵ is —CH₃.
Even more particularly, the present invention provides such compounds of formula I wherein
one of $X^1$ and $X^2$ is hydrogen and the other is —CF₃;
$R^1$ and $R^2$ are each methyl.
Even more particularly, the present invention provides such compounds of formula I wherein
one of $X^1$ and $X^2$ is hydrogen and the other is —OCF₃;
$R^1$ and $R^2$ are each methyl.
Even more particularly, the present invention provides such compounds of formula I wherein
$X^1$ and $X^2$ are each hydrogen;
$R^1$ and $R^2$ are each methyl.
Even more particularly, the present invention provides such compounds of formula I wherein
one of $X^1$ and $X^2$ is hydrogen and the other is t-butyl
$R^1$ and $R^2$ are each methyl.
Even more particularly, the present invention provides such compounds of formula I wherein
one of $X^1$ and $X^2$ is hydrogen and the other is —OCH₃;
$R^1$ and $R^2$ are each methyl.
Even more particularly, the present invention provides such compounds of formula I wherein
$X^1$ and $X^2$ are each —CF₃;
$R^1$ and $R^2$ are each methyl.
Even more particularly, the present invention provides such compounds of formula I wherein $X^1$ and $X^2$ are each —OCH₃;
$R^1$ and $R^2$ are each methyl.
Even more particularly, the present invention provides such compounds of formula I wherein
one of $X^1$ and $X^2$ is hydrogen and the other is halo;
$R^1$ and $R^2$ are each methyl.
Another aspect of the present invention provides methods of treating atherosclerosis, obesity, overweight condition, hypertriglyceridemia, hyperlipidemia, hypoalphalipoproteinemia, dyslipidemia, metabolic syndrome, diabetes mellitus (especially Type II), hyperinsulinemia, impaired glucose tolerance, insulin resistance, diabetic complications, hypertension, coronary heart disease, peripheral vascular disease, hypercholesterolemia, inflammation, osteoporosis, thrombosis or congestive heart failure in a mammal (including a human being) which comprise administering to said mammal a therapeutically effective amount of a compound of Formula I, a prodrug of said compound, or a pharmaceutically acceptable salt of said compound or prodrug. The present invention also provides methods of inducing weight loss in a mammal (including a human being) which comprise administering to said mammal a therapeutically effective amount of a compound of Formula I, a prodrug of said compound, or a pharmaceutically acceptable salt of said compound or prodrug.

Yet another aspect of the present invention provides to methods for treating atherosclerosis in a mammal (including a human being) by administering to a mammal in need of such treatment an atherosclerotic-treating amount of a Formula I compound, a prodrug thereof, or a pharmaceutically acceptable salt of said compound or of said prodrug.

Yet another aspect of the present invention provides methods for treating obesity in a mammal (including a human being) by administering to a mammal in need of such treatment an obesity-treating amount of a Formula I compound, a prodrug thereof, or a pharmaceutically acceptable salt of said compound or of said prodrug.

Yet another aspect of the present invention provides methods for inducing weight loss in a mammal (including a human being) by administering to a mammal a therapeutically effective amount of a Formula I compound, a prodrug of thereof, or a pharmaceutically acceptable salt of thereof said compound or of said prodrug.

Yet another aspect of the present invention provides methods for treating an overweight condition in a mammal (including a human being) by administering to a mammal in need of such treatment an overweight condition-treating amount of a Formula I compound, a prodrug thereof, or a pharmaceutically acceptable salt of said compound or of said prodrug.

Yet another aspect of the present invention provides methods for treating hypertriglyceridemia in a mammal (including a human being) by administering to a mammal in need of such treatment a hypertriglyceridemia-treating amount of a Formula I compound, a prodrug thereof, or a pharmaceutically acceptable salt of said compound or of said prodrug.

Yet another aspect of the present invention provides methods for treating hyperlipidemia in a mammal (including a human being) by administering to a mammal in need of such treatment a hyperlipidemia-treating amount of a Formula I compound, a prodrug thereof, or a pharmaceutically acceptable salt of said compound or of said prodrug.

Yet another aspect of the present invention provides methods for treating hypoalphalipoproteinemia in a mammal (including a human being) by administering to a mammal in need of such treatment a hypoalphalipoproteinemia-treating amount of a Formula I compound, a prodrug thereof, or a pharmaceutically acceptable salt of said compound or of said prodrug.

Yet another aspect of the present invention provides methods for treating metabolic syndrome in a mammal (including a human being) by administering to a mammal in need of such treatment a metabolic syndrome-treating amount of a Formula I compound, a prodrug thereof, or a pharmaceutically acceptable salt of said compound or of said prodrug.

Yet another aspect of the present invention provides methods for treating diabetes mellitus (especially Type II) in a mammal (including a human being) by administering to a mammal in need of such treatment a diabetes mellitus-treating amount of a Formula I compound, a prodrug thereof, or a pharmaceutically acceptable salt of said compound or of said prodrug.

Yet another aspect of the present invention provides methods for treating hyperinsulinemia in a mammal (including a human being) by administering to a mammal in need of such treatment a hyperinsulinemia-treating amount of a Formula I compound, a prodrug thereof, or a pharmaceutically acceptable salt of said compound or of said prodrug.

Yet another aspect of the present invention provides methods for treating impaired glucose tolerance in a mammal (including a human being) by administering to a mammal in need of such treatment an impaired glucose tolerance disease-treating amount of a Formula I compound, a prodrug thereof, or a pharmaceutically acceptable salt of said compound or of said prodrug.

Yet another aspect of the present invention provides methods for treating insulin resistance in a mammal (including a human being) by administering to a mammal in need of such treatment an insulin resistance-treating amount of a Formula I compound, a prodrug thereof, or a pharmaceutically acceptable salt of said compound or of said prodrug.

Yet another aspect of the present invention provides methods for treating diabetic complications (e.g., neuropathy, nephropathy, retinopathy or cataracts) in a mammal (including a human being) by administering to a mammal in need of such treatment a diabetic complications-treating amount of a Formula I compound, a prodrug thereof, or a pharmaceutically acceptable salt of said compound or of said prodrug.

Yet another aspect of the present invention provides methods for treating hypertension in a mammal (including a human being) by administering to a mammal in need of such treatment a hypertension-treating amount of a Formula I compound, a prodrug thereof, or a pharmaceutically acceptable salt of said compound or of said prodrug.

Yet another aspect of the present invention provides methods for treating coronary heart disease in a mammal (including a human being) by administering to a mammal in need of such treatment a coronary heart disease-treating amount of a Formula I compound, a prodrug thereof, or a pharmaceutically acceptable salt of said compound or of said prodrug.

Yet another aspect of the present invention provides methods for treating hypercholesterolemia in a mammal (including a human being) by administering to a mammal in need of such treatment a hypercholesterolemia-treating amount of a Formula I compound, a prodrug thereof, or a pharmaceutically acceptable salt of said compound or of said prodrug.

Yet another aspect of the present invention provides methods for treating inflammation in a mammal (including a human being) by administering to a mammal in need of such treatment an inflammation-treating amount of a Formula I compound, a prodrug thereof, or a pharmaceutically acceptable salt of said compound or of said prodrug.

Yet another aspect of the present invention provides methods for treating osteoporosis in a mammal (including a human being) by administering to a mammal in need of such treatment an osteoporosis-treating amount of a Formula I compound, a prodrug thereof, or a pharmaceutically acceptable salt of said compound or of said prodrug.

Yet another aspect of the present invention provides methods for treating congestive heart failure in a mammal (including a human being) by administering to a mammal in need of such treatment a congestive heart failure-treating amount of a Formula I compound, a prodrug thereof, or a pharmaceutically acceptable salt of said compound or of said prodrug.

A dosage range for the compounds of the present invention is about 0.001 to about 100 mg/kg/day of a Formula I compound, a prodrug thereof, or a pharmaceutically acceptable salt of said compound or of said prodrug. More particularly, the dosage range for the compounds of the present invention is about 0.005 to about 5 mg/kg/day of a Formula I compound, a prodrug thereof, or a pharmaceutically acceptable salt of said compound or of said prodrug.

The present invention also provides pharmaceutical compositions, which comprise a compound of Formula I, a prodrug thereof, or a pharmaceutically acceptable salt of said compound or of said prodrug and a pharmaceutically acceptable vehicle, carrier or diluent. Preferably the composition comprises a therapeutically effective amount of the Formula I compound.

The present invention also provides pharmaceutical compositions for the treatment of atherosclerosis, obesity, an overweight condition, hypertriglyceridemia, hyperlipidemia, hypoalphalipoproteinemia, metabolic syndrome, diabetes mellitus (especially Type II), hyperinsulinemia, impaired glucose tolerance, insulin resistance, diabetic complications, hypertension, thrombosis, coronary heart disease, hypercholesterolemia, inflammation, osteoporosis or congestive heart failure in a mammal (including a human being) which comprise a therapeutically effective amount of a compound of Formula I, a prodrug thereof, or a pharmaceutically acceptable salt of said compound or of said prodrug and a pharmaceutically acceptable vehicle, diluent or carrier.

The present invention also provides pharmaceutical combination compositions comprising: a therapeutically effective amount of a composition comprising
  a first compound, said first compound being a Formula I compound, a prodrug thereof, or a pharmaceutically acceptable salt of said compound or of said prodrug;
  a second compound, said second compound being a lipase inhibitor, an HMG-CoA reductase inhibitor, an HMG-CoA synthase inhibitor, an HMG-CoA reductase gene expression inhibitor, an HMG-CoA synthase gene expression inhibitor, a microsomal triglyceride transfer protein (MTP)/Apo B secretion inhibitor, a cholesterol ester transfer protein (CETP) inhibitor, PPARγ agonists, PPARβ agonists, a bile acid absorption inhibitor, a cholesterol absorption inhibitor, a cholesterol synthesis inhibitor, a squalene synthetase inhibitor, a squalene epoxidase inhibitor, a squalene cyclase inhibitor, a combined squalene epoxidase/squalene cyclase inhbitior, a fibrate, niacin, a combination of niacin and lovastatin, an ion-exchange resin, an antioxidant, an acyl-CoA:cholesterol acyl transferase (ACAT) inhibitor or a bile acid sequestrant; and/or optionally a pharmaceutically acceptable vehicle, diluent or carrier.

Specific embodiments of the second compounds are an HMG-CoA reductase inhibitor and a CETP inhibitor.

Specific embodiments of the HMG-CoA reductase inhibitors are lovastatin, rosuvastatin, pitavastatin, simvastatin, pravastatin, fluvastatin, atorvastatin and cerivastatin, or a pharmaceutically acceptable salt thereof.

Specific embodiments of the CETP inhibitor include, for example, [2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester.

In another aspect, the present invention provides methods for treating atherosclerosis in a mammal comprising administering to a mammal suffering from atherosclerosis:
  a first compound, said first compound being a Formula I compound, a prodrug thereof, or a pharmaceutically acceptable salt of said compound or of said prodrug; and
  a second compound, said second compound being a lipase inhibitor, an HMG-CoA reductase inhibitor, an HMG-CoA synthase inhibitor, an HMG-CoA reductase gene expression inhibitor, an HMG-CoA synthase gene expression inhibitor, a MTP/Apo B secretion inhibitor, a CETP inhibitor, PPARγ agonists, PPARβ agonists, a bile acid absorption inhibitor, a cholesterol absorption inhibitor, a cholesterol synthesis inhibitor, a squalene synthetase inhibitor, a squalene epoxidase inhibitor, a squalene cyclase inhibitor, a combined squalene epoxidase/squalene cyclase inhibitor, a fibrate, niacin, a combination of niacin and lovastatin, an ion-exchange resin, an antioxidant, an ACAT inhibitor or a bile acid sequestrant wherein the amounts of the first and second compounds result in a therapeutic effect.

One embodiment of the above methods is wherein the second compound is an HMG-CoA reductase inhibitor or a CETP inhibitor.

Another embodiment of the above methods is wherein the HMG-CoA reductase inhibitor is lovastatin, rosuvastatin, pitavastatin, simvastatin, pravastatin, fluvastatin, atorvastatin or cerivastatin or a pharmaceutically acceptable salt thereof.

Specific embodiments of the CETP inhibitor include, for example, [2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester.

In another aspect, the present invention provides kits comprising:
  a. a first compound, said first compound being a Formula I compound, a prodrug thereof, or a pharmaceutically acceptable salt of said compound or of said prodrug and a pharmaceutically acceptable carrier, vehicle or diluent in a first unit dosage form;
  b. a second compound, said second compound being a lipase inhibitor, an HMG-CoA reductase inhibitor, an HMG-CoA synthase inhibitor, an HMG-CoA reductase gene expression inhibitor, an HMG-CoA synthase gene expression inhibitor, an MTP/Apo B secretion inhibitor, a CETP inhibitor, PPARγ agonists, PPARβ agonists, a bile acid absorption inhibitor, a cholesterol absorption inhibitor, a cholesterol synthesis inhibitor, a squalene synthetase inhibitor, a squalene epoxidase inhibitor, a squalene cyclase inhibitor, a combined squalene epoxidase/squalene cyclase inhibitor, a fibrate, niacin, a combination of niacin and lovastatin, an ion-exchange resin, an antioxidant, an ACAT inhibitor or a bile acid sequestrant and a pharmaceutically acceptable carrier, vehicle or diluent in a second unit dosage form;
  c. means for containing said first and second dosage forms wherein the amounts of the first and second compounds result in a therapeutic effect.

An embodiment of the second compound is an HMG-CoA reductase inhibitor or a CETP inhibitor.

An embodiment of the HMG-CoA reductase inhibitor is lovastatin, rosuvastatin, pitavastatin, simvastatin, pravastatin, fluvastatin, atorvastatin or cerivastatin or pharmaceutically acceptable salts thereof.

Specific embodiments of the CETP inhibitor include, for example, [2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester.

The present invention also provides pharmaceutical combination compositions comprising: a therapeutically effective amount of a composition comprising
  a first compound, said first compound being a Formula I compound, a prodrug thereof, or a pharmaceutically acceptable salt of said compound or of said prodrug;
  a second compound, said second compound being a diabetic-treating agent selected from aldose reductase inhibitors, glucocorticoid receptor antagonists, glycogenolysis inhibitors, glycogen phosphorylase inhibitors, sorbitol dehydrogenase inhibitors, insulin, insulin analogs, insulinotropin, sulfonylureas, sulfonylureas analogs, biguanides, imidazolines, insulin secretagogues, linogliride, glitazones, non-glitazone PPARγ agonists, PPARγ agonists, glucosidase inhibitors, acarbose, miglitol, emiglitate, voglibose, camiglibose, β-agonists, phosphodiesterase inhibitors, vanadate, vanadium complexes (e.g. Naglivan®), peroxovanadium complexes, amylin antagonists, glucagon antagonists, gluconeogenesis inhibitors, somatostatin analogs, antilipolytic agents, nicotinic acid, acipimox, pramlintide (Symlin™), and nateglinide; and/or optionally
  a pharmaceutical vehicle, diluent or carrier.

Particular embodiments among the second compounds are chlorpropamide, glibenclamide, tolbutamide, tolazamide, acetohexamide, Glypizide®, glimepiride, repaglinide, meglitinide, mefformin, phenformin, buformin, midaglizole, isaglidole, deriglidole, idazoxan, efaroxan, fluparoxan, ciglitazone, pioglitazone, rosiglitazone, englitazone, darglitazone, clomoxir and etomoxir.

More particular embodiments of the second compounds are glibenclamide, Glypizide®, glimepiride, repaglinide, metformin, and pioglitazone.

In another aspect, the present invention provides methods for treating diabetes in a mammal comprising administering to a mammal suffering from diabetes
  a first compound, said first compound being a Formula I compound a prodrug thereof, or a pharmaceutically acceptable salt of said compound or of said prodrug; and
  a second compound, said second compound being a diabetic treating agent selected from aldose reductase inhibitors, glucocorticoid receptor antagonists, glycogenolysis inhibitors, glycogen phosphorylase inhibitors, sorbitol dehydrogenase inhibitors, insulin, insulin analogs, insulinotropin, sulfonylureas and analogs, biguanides, imidazolines, insulin secretagogues, linogliride, glitazones, non-glitazone PPARγ agonists, PPARβ agonists, α-glucosidase inhibitors, acarbose, miglitol, emiglitate, voglibose, camiglibose, β-agonists, phosphodiesterase inhibitors, vanadate, vanadium complexes (e.g. Naglivan®), peroxovanadium complexes, amylin antagonists, glucagon antagonists, gluconeogenesis inhibitors, somatostatin analogs, antilipolytic agents, nicotinic acid, acipimox, pramlintide (Symlin™), and nateglinide wherein the amounts of the first and second compounds result in a therapeutic effect.

A particular embodiment of the above methods is wherein the second compound is chlorpropamide, glibenclamide, tolbutamide, tolazamide, acetohexamide, Glypizide®, glimepiride, repaglinide, meglitinide, metformin, phenformin, buformin, midaglizole, isaglidole, deriglidole, idazoxan, efaroxan, fluparoxan, ciglitazone, pioglitazone, englitazone, darglitazone, clomoxir or etomoxir.

A particular embodiment of the above methods is wherein the second compound is glibenclamide, Glypizide®, glimepiride, repaglinide, metformin, pioglitazone or rosiglitazone.

In another aspect, the present invention provides kits comprising:
  a. a first compound, said first compound being a Formula I compound, a prodrug thereof, or a pharmaceutically acceptable salt of said compound or of said prodrug and a pharmaceutically acceptable vehicle, diluent or carrier in a first unit dosage form;
  b. a second compound, said second compound being a diabetic treating agent selected from aldose reductase inhibitors, glucocorticoid receptor antagonists, glycogenolysis inhibitors, glycogen phosphorylase inhibitors, sorbitol dehydrogenase inhibitors, insulin, insulin analogs, insulinotropin, sulfonylureas and analogs, biguanides, imidazolines, insulin secretagogues, linogliride, glitazones, non-glitazone PPARγ agonists, PPARβ agonists, glucosidase inhibitors, acarbose, miglitol, emiglitate, voglibose, camiglibose, β-agonists, phosphodiesterase inhibitors, vanadate, vanadium complexes (e.g. Naglivan®), peroxovanadium complexes, amylin antagonists, glucagon antagonists, gluconeogenesis inhibitors, somatostatin analogs, antilipolytic agents, nicotinic acid, acipimox, pramlintide (Symlin™), and nateglinide and a pharmaceutically acceptable vehicle, diluent or carrier in a second unit dosage form; and
  c. means for containing said first and second dosage forms wherein the amounts of the first and second compounds result in a therapeutic effect.

An embodiment of the second compound is chlorpropamide, glibenclamide, tolbutamide, tolazamide, acetohexamide, Glypizide®, glimepiride, repaglinide, meglitinide, metformin, phenformin, buformin, midaglizole, isaglidole, deriglidole, idazoxan, efaroxan, fluparoxan, ciglitazone, pioglitazone, rosiglitazone, englitazone, darglitazone, clomoxir or etomoxir.

A particular embodiment of the second compound is glibenclamide, Glypizide®, glimepiride, repaglinide, metformin, pioglitazone or rosiglitazone.

The present invention also provides pharmaceutical combination compositions comprising: a therapeutically effective amount of a composition comprising
  a first compound, said first compound being a Formula I compound, a prodrug thereof, or a pharmaceutically acceptable salt of said compound or of said prodrug;
  a second compound, said second compound being phenylpropanolamine, ephedrine, pseudoephedrine, phentermine, a neuropeptide Y antagonist, a $\beta_3$-adrenergic receptor agonist, an apolipoprotein-B secretion/microsomal triglyceride transfer protein (apo-B/MTP) inhibitor, an MCR-4 agonist, a cholecystokinin-A agonist, a monoamine reuptake inhibitor, a sympathomimetic agent, a serotoninergic agent, a dopamine agonist, a melanocyte-stimulating hormone receptor agonist or mimetic, a 5HT2c agonist, a melanocyte-stimulating hormone receptor analog, a cannabinoid receptor antagonist, a melanin concentrating hormone antagonist, leptin, the OB protein, a leptin analog, a leptin receptor agonist, a galanin antagonist, a lipase inhibitor, an anorectic agent, a bombesin agonist, a neuropeptide-Y antagonist, thyroxine, a thyromimetic agent, dehydroepiandrosterone or an analog thereof, a glucocorticoid receptor modulator, an orexin receptor antagonist, a urocortin binding protein antagonist, a glucagon-like peptide-1 receptor agonist, a ciliary neurotrophic factor, a human agouti-related protein (AGRP), a ghrelin receptor antagonist, histamine 3 receptor antagonist or inverse agonist, or a neuromedin U receptor agonist; and/or optionally
  a pharmaceutical vehicle, diluent or carrier.

Specific embodiments of the second compounds are orlistat, sibutramine and bromocriptine.

In another aspect, the present invention provides methods for treating obesity in a mammal comprising administering to a mammal suffering from obesity
  a first compound, said first compound being a Formula I compound a prodrug thereof, or a pharmaceutically acceptable salt of said compound or of said prodrug; and
  a second compound, said second compound being phenylpropanolamine, ephedrine, pseudoephedrine, phentermine, a neuropeptide Y antagonist, a $\beta_3$-adrenergic receptor agonist, an apolipoprotein-B secretion/microsomal triglyceride transfer protein (apo-B/MTP) inhibitor, an MCR-4 agonist, a cholecystokinin-A agonist, a monoamine reuptake inhibitor, a sympathomimetic agent, a serotoninergic agent, a dopamine agonist, a melanocyte-stimulating hormone receptor agonist or mimetic, a 5HT2c agonist, a melanocyte-stimulating hormone receptor analog, a cannabinoid receptor antagonist, a melanin concentrating hormone antagonist, leptin, the OB protein, a leptin analog, a leptin receptor agonist, a galanin antagonist, a lipase inhibitor, an anorectic agent, a bombesin agonist, a neuropeptide-Y antagonist, thyroxine, a thyromimetic agent, dehydroepiandrosterone or an analog thereof, a glucocorticoid receptor modulator, an orexin receptor antagonist, a urocortin binding protein antagonist, a glucagon-like peptide-1 receptor agonist, a ciliary neurotrophic factor, a human agouti-related protein (AGRP), a ghrelin receptor antagonist, histamine 3 receptor antagonist or inverse agonist, or a neuromedin U receptor agonist; wherein the amounts of the first and second compounds result in a therapeutic effect.

An embodiment of the above methods is wherein the second compound is orlistat, sibutramine or bromocriptine.

In another aspect, the present invention provides kits comprising:
  a. a first compound, said first compound being a Formula I compound, a prodrug thereof, or a pharmaceutically acceptable salt of said compound or of said prodrug and a pharmaceutically acceptable carrier, vehicle or diluent in a first unit dosage form;
  b. a second compound, said second compound being phenylpropanolamine, ephedrine, pseudoephedrine, phentermine, a neuropeptide Y antagonist, a $\beta_3$-adrenergic receptor agonist, an apolipoprotein-B secretion/microsomal triglyceride transfer protein (apo-B/MTP)

inhibitor, an MCR-4 agonist, a cholecystokinin-A agonist, a monoamine reuptake inhibitor, a sympathomimetic agent, a serotoninergic agent, a dopamine agonist, a melanocyte-stimulating hormone receptor agonist or mimetic, a 5HT2c agonist, a melanocyte-stimulating hormone receptor analog, a cannabinoid receptor antagonist, a melanin concentrating hormone antagonist, leptin, the OB protein, a leptin analog, a leptin receptor agonist, a galanin antagonist, a lipase inhibitor, an anorectic agent, a bombesin agonist, a neuropeptide-Y antagonist, thyroxine, a thyromimetic agent, dehydroepiandrosterone or an analog thereof, a glucocorticoid receptor modulator, an orexin receptor antagonist, a urocortin binding protein antagonist, a glucagon-like peptide-1 receptor agonist, a ciliary neurotrophic factor, a human agouti-related protein (AGRP), a ghrelin receptor antagonist, histamine 3 receptor antagonist or inverse agonist, or a neuromedin U receptor agonist; or a pharmaceutically acceptable vehicle, diluent or carrier in a second unit dosage form; and c. means for containing said first and second dosage forms wherein the amounts of the first and second compounds result in a therapeutic effect.

An embodiment of the second compound is orlistat, sibutramine or bromocriptine.

The present invention also provides pharmaceutical combination compositions comprising: a therapeutically effective amount of a composition comprising a first compound, said first compound being a Formula I compound, a prodrug thereof, or a pharmaceutically acceptable salt of said compound or of said prodrug;

a second compound, said second compound being an anti-hypertensive agent; and/or optionally a pharmaceutical vehicle, diluent or carrier.

Specific embodiments of anti-hypertensive agents are a calcium channel blocker, an angiotensin converting enzyme (ACE) inhibitor and a diuretic.

In another aspect, the present invention provides methods for treating hypertension in a mammal comprising administering to a mammal suffering from hypertension a first compound, said first compound being a Formula I compound a prodrug thereof, or a pharmaceutically acceptable salt of said compound or of said prodrug; and a second compound, said second compound being an antihypertensive agent wherein the amounts of the first and second compounds result in a therapeutic effect.

Embodiments of the anti-hypertensive agents are a calcium channel blocker, an angiotensin converting enzyme (ACE) inhibitor and a diuretic.

In another aspect, the present invention provides kits comprising:

a. a first compound, said first compound being a Formula I compound, a prodrug thereof, or a pharmaceutically acceptable salt of said compound or of said prodrug and a pharmaceutically acceptable carrier, vehicle or diluent in a first unit dosage form;

b. a second compound, said second compound being an anti-hypertensive agent and a pharmaceutically acceptable vehicle, diluent or carrier in a second unit dosage form; and c. means for containing said first and second dosage forms wherein the amounts of the first and second compounds result in a therapeutic effect.

Embodiments of anti-hypertensive agents are a calcium channel blocker, an angiotensin converting enzyme (ACE) inhibitor and a diuretic.

The present invention also provides pharmaceutical combination compositions comprising: a therapeutically effective amount of a composition comprising a first compound, said first compound being a Formula I compound, a prodrug thereof, or a pharmaceutically acceptable salt of said compound or of said prodrug;

a second compound, said second compound being an anti-osteoporosis agent; and/or optionally a pharmaceutical vehicle, diluent or carrier.

Specific embodiments of anti-osteoporosis agents are selective estrogen agonists/antagonists, such as lasofoxifene, raloxifene, TSE-424 and arazoxifene, and bisphosphonates, such as alendronate and resindronate.

In another aspect, the present invention provides methods for treating osteoporosis in a mammal comprising administering to a mammal suffering from osteoporosis a first compound, said first compound being a Formula I compound a prodrug thereof, or a pharmaceutically acceptable salt of said compound or of said prodrug; and a second compound, said second compound being an anti-osteoporosis agent wherein the amounts of the first and second compounds result in a therapeutic effect.

Embodiments of anti-osteporosis agents are selective estrogen agonists/antagonists, such as lasofoxifene, raloxifene, TSE-424 and arazoxifene, and bisphosphonates, such as alendronate and resindronate.

In another aspect, the present invention provides kits comprising:

a. a first compound, said first compound being a Formula I compound, a prodrug thereof, or a pharmaceutically acceptable salt of said compound or of said prodrug and a pharmaceutically acceptable carrier, vehicle or diluent in a first unit dosage form;

b. a second compound, said second compound being an anti-osteoporosis agent and a pharmaceutically acceptable vehicle, diluent or carrier in a second unit dosage form; and c. means for containing said first and second dosage forms wherein the amounts of the first and second compounds result in a therapeutic effect.

Embodiments of anti-osteporosis agents are selective estrogen agonists/antagonists, such as lasofoxifene, raloxifene, TSE-424 and arazoxifene, and bisphosphonates, such as alendronate and resindronate.

The term "treating", "treat" or "treatment" as used herein includes preventative (e.g., prophylactic) and palliative treatment.

By "pharmaceutically acceptable" is meant the carrier, diluent, vehicle, excipient, and/or salt must be compatible with the other ingredients of the formulation, and not deleterious to the recipient thereof.

As used herein, "therapeutically effective amount of a compound" means an amount that is effective to exhibit therapeutic or biological activity at the site(s) of activity in a mammalian subject, without undue adverse side effects (such as undue toxicity, irritation or allergic response), commensurate with a reasonable benefit/risk ratio when used in the manner of the present invention.

The compound(s) of the present invention shall include all active forms of such compound(s), including, for example, the free form thereof, e.g., the free acid or base form, and also, all prodrugs, polymorphs, hydrates, solvates, tautomers, stereoisomers, e.g., diastereomers and enantiomers, and the like, and all pharmaceutically acceptable salts as described above, unless specifically stated otherwise. It will also be appreciated that suitable active metabolites of such compound(s), in any suitable form, are also included herein.

Metabolic syndrome, also known as Syndrome X, refers to a common clinical disorder that is defined as the presence of increased insulin concentrations in association with other disorders including viceral obesity, hyperlipidemia, dyslipidemia, hyperglycemia, hypertension, and potentially hyperuricemis and renal dysfunction.

The expression "prodrug" refers to compounds that are drug precursors which following administration release the drug in vivo via some chemical or physiological process (e.g., a prodrug on being brought to the physiological pH or through enzyme action is converted to the desired drug form). Exemplary prodrugs upon cleavage release the corresponding free acid, and such hydrolyzable ester-forming residues of the Formula I compounds include but are not limited to those having a carboxyl moiety wherein the free hydrogen is replaced by ($C_1$–$C_4$)alkyl, ($C_2$–$C_7$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N-($C_1$–$C_2$)alkylamino($C_2$–$C_3$)alkyl (such as β-dimethylaminoethyl), carbamoyl-($C_1$–$C_2$)alkyl, N,N-di($C_1$–$C_2$) alkylcarbamoyl-($C_1$–$C_2$)alkyl and piperidino-, pyrrolidino- or morpholino($C_2$–$C_3$)alkyl.

The term het refers to an optionally substituted 5-, 6- or 7-membered saturated, partially saturated or unsaturated heterocyclic ring containing from 1 to 3 heteroatoms selected from the group consisting of nitrogen, oxygen and sulfur; and including any bicyclic group in which any of the above heterocyclic rings is fused to a benzene ring or another heterocyclic ring; and the nitrogen atom may be in the oxidized state giving the N-oxide form; and substituted by 0 to 3 independent substituents.

By alkenyl is meant straight chain unsaturated hydrocarbon or branched chain unsaturated hydrocarbon. Exemplary of such groups (assuming the designated length encompasses the particular example) are ethenyl, propenyl, butenyl, pentenyl, hexenyl and heptenyl, and all isomeric forms and straight and branched forms thereof.

By halo is meant fluoro, chloro, bromo or iodo.

By alkyl is meant straight chain saturated hydrocarbon or branched chain saturated hydrocarbon. Exemplary of such alkyl groups (assuming the designated length encompasses the particular example) are methyl, ethyl, propyl, isopropyl, butyl, sec-butyl, tertiary butyl, pentyl, isopentyl, neopentyl, tertiary pentyl, 1-methylbutyl, 2-methylbutyl, 3-methylbutyl, hexyl, isohexyl, heptyl and octyl. This term also includes a saturated hydrocarbon (straight chain or branched) wherein a hydrogen atom is removed from each of the terminal carbons.

By alkoxy is meant straight chain saturated alkyl or branched chain saturated alkyl bonded through an oxy. Exemplary of such alkoxy groups (assuming the designated length encompasses the particular example) are methoxy, ethoxy, propoxy, isopropoxy, butoxy, isobutoxy, tertiary butoxy, pentoxy, isopentoxy, neopentoxy, tertiary pentoxy, hexoxy, isohexoxy, heptoxy and octoxy.

The carbon atom content of various hydrocarbon-containing moieties is indicated by a prefix designating the minimum and maximum number of carbon atoms in the moiety, i.e., the prefix $C_i$–$C_j$ indicates a moiety of the integer "i" to the integer "j" carbon atoms, inclusive. Thus, for example, $C_1$–$C_3$ alkyl refers to alkyl of one to three carbon atoms, inclusive, or methyl, ethyl, propyl and isopropyl, and all isomeric forms and straight and branched forms thereof.

By aryl is meant an optionally substituted six-membered aromatic ring, including polyaromatic rings. Examples of aryl include phenyl, naphthyl and biphenyl.

It is understood herein that if a carbocyclic or heterocyclic moiety may be bonded or otherwise attached to a designated substrate through differing ring atoms without denoting a specific point of attachment, then all possible points are intended, whether through a carbon atom or, for example, a trivalent nitrogen atom. For example, the term "pyridyl" means 2-, 3- or 4-pyridyl, the term "thienyl" means 2- or 3-thienyl, and so forth.

The expression "pharmaceutically-acceptable salt" refers to nontoxic anionic salts containing anions such as (but not limited to) chloride, bromide, iodide, sulfate, bisulfate, phosphate, acetate, maleate, fumarate, oxalate, lactate, tartrate, citrate, gluconate, methanesulfonate and 4-toluenesulfonate. The expression also refers to nontoxic cationic salts such as (but not limited to) sodium, potassium, calcium, magnesium, ammonium or protonated benzathine (N,N'-dibenzylethylenediamine), choline, ethanolamine, diethanolamine, ethylenediamine, meglamine (N-methyl-glucamine), benethamine (N-benzylphenethylamine), piperazine or tromethamine (2-amino-2-hydroxymethyl-1,3-propanediol).

As used herein, the expressions "reaction-inert solvent" and "inert solvent" refers to a solvent or a mixture thereof which does not interact with starting materials, reagents, intermediates or products in a manner which adversely affects the yield of the desired product.

The chemist of ordinary skill will recognize that certain compounds of the present invention will contain one or more atoms, which may be in a particular stereochemical or geometric configuration, giving rise to stereoisomers and configurational isomers. All such isomers and mixtures thereof are included in the present invention. Hydrates and solvates of the compounds of the present invention are also included.

The present invention also includes isotopically-labeled compounds, which are structurally identical to those disclosed herein, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, sulfur, fluorine and chlorine, such as $^2$H, $^3$H, $^{13}$C, $^{14}$C, $^{15}$N, $^{18}$O, $^{17}$O, $^{35}$S, $^{18}$F and $^{36}$Cl, respectively. Compounds of the present invention, prodrugs thereof, and pharmaceutically acceptable salts of said compounds and of said prodrugs which contain the aforementioned isotopes and/or other isotopes of other atoms are within the scope of this invention. Certain isotopically labeled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, may afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out known or referenced procedures and by substituting a readily available isotopically labeled reagent for a non-isotopically labeled reagent.

All patents and patent applications referred to herein are hereby incorporated by reference.

DTT means dithiothreitol. DMSO means dimethyl sulfoxide. EDTA means ethylenediamine tetraacetic acid.

DETAILED DESCRIPTION OF THE INVENTION

In general the compounds of the present invention can be made by processes, which include processes analogous to those known in the chemical arts, particularly in light of the description contained herein. Certain processes for the manufacture of the compounds of the present invention are provided as further features of this invention and are illustrated by the following reaction schemes. Other processes are described in the experimental section.

As an initial note, in the preparation of the Formula I compounds, it is noted that some of the preparation methods useful for the preparation of the compounds described herein may require protection of remote functionality (e.g., primary amine, secondary amine, carboxyl in Formula I precursors). The need for such protection will vary depending on the nature of the remote functionality and the conditions of the preparative methods and can be readily determined by one of ordinary skill in the art. The use of such protection/deprotection methods is also within the ordinary skill in the art. For a general description of protecting groups and their use, see T. W. Greene, *Protective Groups in Organic Synthesis*, John Wiley & Sons, New York, 1991.

For example, in the reaction schemes below, certain Formula I compounds contain primary amines or carboxylic acid functionalities, which may interfere with reactions at other sites of the molecule if left unprotected. Accordingly, such functionalities may be protected by an appropriate protecting group, which may be removed in a subsequent step. Suitable protecting groups for amine and carboxylic acid protection include those protecting groups commonly used in peptide synthesis (such as N-t-butoxycarbonyl, benzyloxycarbonyl, and 9-fluorenylmethylenoxycarbonyl for amines and lower alkyl or benzyl esters for carboxylic acids) which are generally not chemically reactive under the reaction conditions described and can typically be removed without chemically altering other functionality in the Formula I compound.

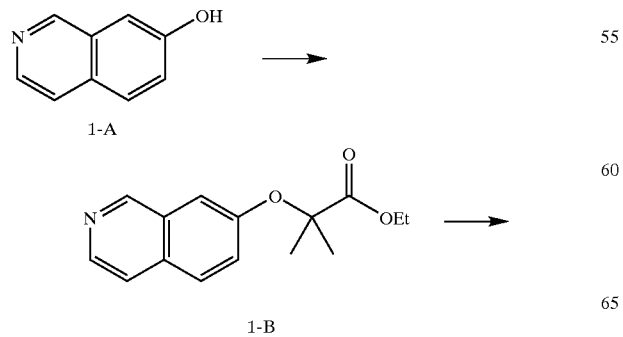

SCHEME 1

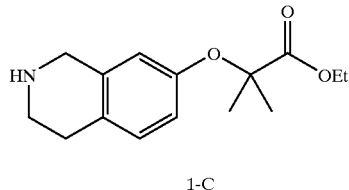

1-C

Scheme 1

7-Hydroxyisoquinoline of formula 1-A, which is commercially available, ethyl 2-bromoisobutyrate and a base, such as potassium carbonate, are mixed in an appropriate solvent, such as DMF. The reaction mixture is heated to a temperature of about 80° C. to about 120° C., preferably about 95° C., under a nitrogen atmosphere for a period of about 14 hours to about 24 hours, preferably about 18 hours, to give the compound of formula 1-B.

The compound of formula 1-B is reduced, using procedures known in the art, to give the compound 1-C. Generally, the compound of formula 1-B is reduced by hydrogenation, preferably at about 50 psi pressure, over a catalyst such as platinum (IV) oxide or Pt/C in an acidic medium such as acetic acid or an acid (such as HCl or $H_2SO_4$) in an alcoholic solvent at a temperature of about 20° C. to about 30° C., preferably about room temperature, for a period of about 14 to about 24 hours, preferably about 18 hours, to give the compound of formula 1-C.

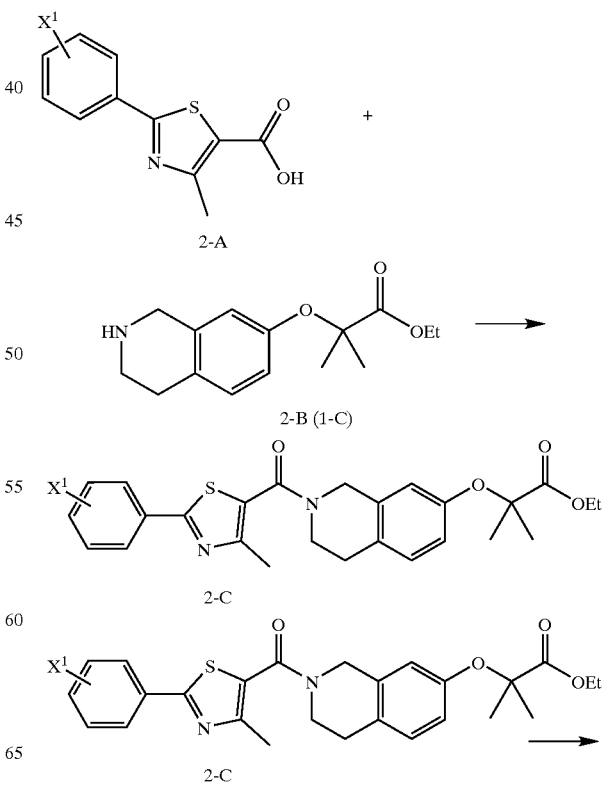

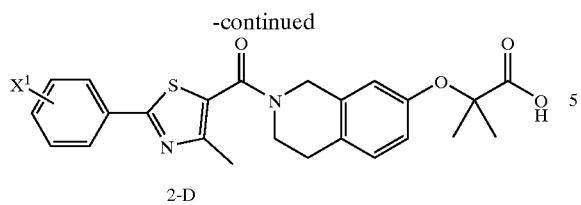

2-D

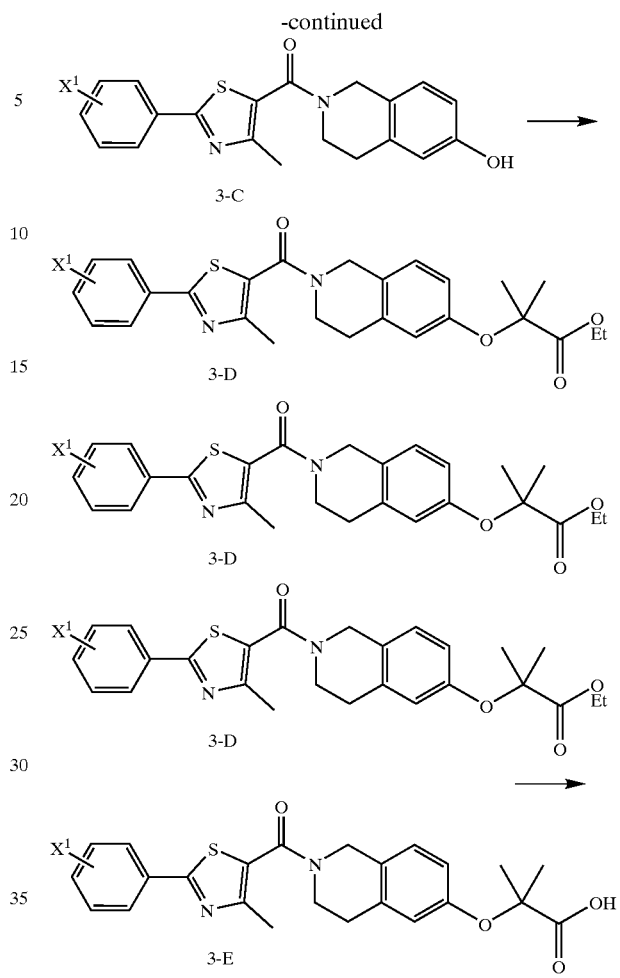

Scheme 2

Oxalyl chloride and a solvent, such as DMF, are added to commercially available 4-methyl-2-(substituted-phenyl)-5-thiazolecarboxylic acid of formula 2-A, wherein $X^1$ is as defined above, in an appropriate solvent, such as methylene chloride, at a temperature of about −5° C. to about 5° C., preferably about 0° C., under a nitrogen atmosphere. The reaction mixture is allowed to warm to room temperature and stirred under a nitrogen atmosphere for a period of about 3 hours to about 6 hours, preferably about 3 hours. The resulting acid chloride is added to the compound of formula 2-B (prepared as the compound of formula 1-C in Scheme 1) in a solvent, such as methylene chloride, and a base, such as triethylamine, at a temperature of about −5° C. to about 5° C., preferably about 0° C., under a nitrogen atmosphere. The reaction mixture is allowed to warm to a temperature of about 20° C. to about 30° C., preferably about room temperature, and stirred under a nitrogen atmosphere for a period of about 14 hours to about 24 hours, preferably about 18 hours, to give the compound of formula 2-C, wherein $X^1$ is as defined above.

The compound of formula 2-C is hydrolyzed to give the compound of formula 2-D. Alternatively, the hydrolysis may be omitted when the ester is a suitable prodrug for the carboxylic acid. Generally, the ester moiety is hydrolyzed in an aqueous alcoholic solvent such as methanol or ethanol and water with a base, such as potassium carbonate, at a temperature of about 80° C. to about 125° C., preferably about 100° C., for a period of about one to four hours, preferably about 90 minutes, to give the corresponding compound of formula 2-D, wherein $X^1$ is as defined above.

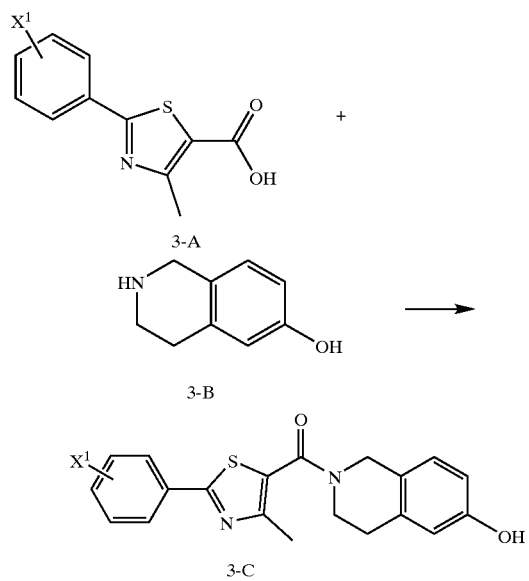

Scheme 3

Commercially available 4-methyl-2-[substituted-phenyl]-5-thiazolecarboxylic acid of formula 3-A where $X^1$ is as defined above, 1-hydroxybenzotriazole and 1-(3-dimethylaminopropyl)-3-ethylcarbodiimide hydrochloride are added to 6-hydroxy-1,2,3,4-tetrahydroisoquinoline hydrobromide of formula 3-B (prepared as described in D. J. Sail and G. L. Grunewald, J. Med. Chem., 1987, 30, 2208) in an appropriate base, such as triethylamine, and a solvent, such as methylene chloride. The reaction mixture is stirred under nitrogen atmosphere at a temperature of about 20° C. to about 30° C., preferably about room temperature, for a period of about 14 to about 24 hours, preferably about 18 hours. The reaction is diluted with a solvent, such as methylene chloride, and made acidic with, e.g., citric acid, to give the compound of formula 3-C, wherein $X^1$ is as defined above.

The compound of formula 3-C is alkylated, using procedures known in the art, to give the compound of formula 3-D, wherein $X^1$ is as defined above. Generally, the compound of formula 3-C, ethyl 2-bromoisobutyrate and a base, such as potassium carbonate, are mixed in an appropriate solvent, such as DMF. The reaction is heated to a temperature of about 80° C. to about 120° C., preferably about 95° C., under a nitrogen atmosphere for a period of about 14 hours to about 24 hours, preferably about 18 hours. The reaction is concentrated under reduced pressure and an appropriate acid, such as hydrochloric acid, is added to give the compound of formula 3-D, wherein $X^1$ is as defined above.

The compound of formula 3-D is hydrolyzed to give the corresponding compound of formula 3-E wherein $X^1$ is as defined above. Alternatively, the hydrolysis may be omitted when the ester is a suitable prodrug for the carboxylic acid. Generally, lithium hydroxide monohydrate in water is added to the compound of formula 3-D in an appropriate solvent, such as THF. The reaction mixture is stirred at a temperature of about 20° C. to about 30° C., preferably about room temperature, for a period of about 14 to about 24 hours, preferably about 18 hours. The reaction is made acidic with an appropriate acid, such as hydrochloric acid, and the solvent, such as THF, is removed under reduced pressure to give the compound of formula 3-E, wherein $X^1$ is as defined above.

4

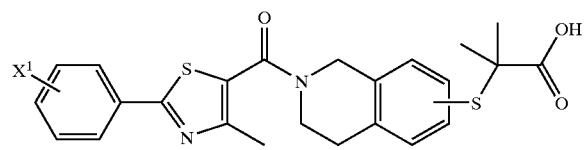

The thiol analogs of formula 4 wherein $X^1$ is as defined above can be prepared from the corresponding 7-mercapto-1,2,3,4-tetrahydroisoquinoline and 6-mercapto-1,2,3,4-tetrahydroisoquinoline by following the procedures of Schemes 1, 2 and 3 above. 7-mercapto-1,2,3,4-tetrahydroisoquinoline can be prepared as described in U.S. Pat. No. 4,228,170, which is hereby incorporated by reference herein. 6-mercapto-1,2,3,4-tetrahydroisoquinoline can be prepared by starting with commercially available 6-amino-1,2,3,4-tetrahydroisoquinoline and following the procedures described in U.S. Pat. No. 4,228,170.

Preparation of compounds of Formula I, with other permutations of the variables as described above, can be conducted using procedures similar to those described in the schemes above. Additional methods to prepare Formula I compounds would be readily known to one of ordinary skill in the art of organic chemistry and may be further exemplified in the literature and in the Preparations and Examples below.

The starting materials and reagents for the above described reaction schemes are readily available or can be easily synthesized by those skilled in the art using conventional methods of organic synthesis. Some of the preparation methods described herein will require protection of remote functionality (i.e., carboxyl). The need for these protecting groups will vary depending on the nature of the remote functionality and the conditions of the preparation methods and can be readily determined by one skilled in the art. For a general description of protecting groups (e.g., halo($C_1$–$C_4$) alkyl, ($C_1$–$C_4$)alkoxymethyl, arylmethyl and tri($C_1$–$C_4$) alkylsilyl) and their use, see T. W. Greene, *Protective Groups in Organic Synthesis*, John Wiley & Sons, New York, 1991.

Prodrugs of the compounds of Formula I can be prepared according to methods analogous to those known to those skilled in the art. Exemplary processes are described below.

Prodrugs of this invention where a carboxyl group in a carboxylic acid of Formula I is replaced by an ester can be prepared by combining the carboxylic acid with the appropriate alkyl halide in the presence of a base such as potassium carbonate in an inert solvent such as dimethylformamide at a temperature of about 0° C. to about 100° C. for about 1 to about 24 hours. Alternatively, the acid is combined with appropriate alcohol as solvent in the presence of a catalytic amount of acid such as concentrated sulfuric acid at a temperature of about 20° C. to about 100° C., preferably at a reflux, for about 1 hour to about 24 hours. Another method is the reaction of the acid with a stoichiometric amount of the alcohol in the presence of a catalytic amount of acid in an inert solvent such as toluene or tetrahydrofuran, with concomitant removal of the water being produced by physical (e.g., Dean-Stark trap) or chemical (e.g., molecular sieves) means.

Prodrugs of this invention where an alcohol function has been derivatized as an ether can be prepared by combining the alcohol with the appropriate alkyl bromide or iodide in the presence of a base such as potassium carbonate in an inert solvent such as dimethylformamide at a temperature of about 0° C. to about 100C for about 1 to about 24 hours. Alkanoylaminomethyl ethers may be obtained by reaction of the alcohol with a bis-(alkanoylamino)methane in the presence of a catalytic amount of acid in an inert solvent such as tetrahydrofuran, according to a method described in U.S. Pat. No. 4,997,984. Alternatively, these compounds may be prepared by the methods described by Hoffman et al. in J. Org. Chem. 1994, 59, 3530.

Glycosides are prepared by reaction of the alcohol and a carbohydrate in an inert solvent such as toluene in the presence of acid. Typically the water formed in the reaction is removed as it is being formed as described above. An alternate procedure is the reaction of the alcohol with a suitably protected glycosyl halide in the presence of base followed by deprotection.

N-(1-hydroxyalkyl) amides and N-(1-hydroxy-1-(alkoxycarbonyl)methyl) amides can be prepared by the reaction of the parent amide with the appropriate aldehyde under neutral or basic conditions (e.g., sodium ethoxide in ethanol) at temperatures between 25° C. and 70° C. N-alkoxymethyl or N-1-(alkoxy)alkyl derivatives can be obtained by reaction of the N-unsubstituted compound with the necessary alkyl halide in the presence of a base in an inert solvent.

The compounds of the present invention can also be used in conjunction with other pharmaceutical agents for the treatment of the diseases/conditions as described herein.

In combination therapy treatment, both the compounds of the present invention and the other drug therapies are administered to mammals (e.g., humans, male or female) by conventional methods. The compounds of the present invention can also be administered in combination with naturally occurring compounds that act to lower plasma cholesterol levels. These naturally occurring compounds are commonly called nutraceuticals and include, for example, garlic extract and niacin. A slow-release form of niacin is available and is known as Niaspan. Niacin may also be combined with other therapeutic agents such as lovastatin, which is an HMG-CoA reductase inhibitor and described further below. This combination therapy is known as ADVICOR™ (Kos Pharmaceuticals Inc.).

Any cholesterol absorption inhibitor can be used as the second compound in the combination aspect of the present invention. The term cholesterol absorption inhibition refers to the ability of a compound to prevent cholesterol contained within the lumen of the intestine from entering into the intestinal cells and/or passing from within the intestinal cells into the blood stream. Such cholesterol absorption inhibition activity is readily determined by those skilled in the art according to standard assays (e.g., J. Lipid Res. (1993) 34: 377–395). Cholesterol absorption inhibitors are known to those skilled in the art and are described, for example, in PCT WO 94/00480. An example of a recently approved cholesterol absorption inhibitor is ZETIA™ (ezetimibe) (Merck/Schering-Plough).

Any HMG-CoA reductase inhibitor can be used as the second compound in the combination aspect of the present invention. The term HMG-CoA reductase inhibitor refers to compounds, which inhibit the bioconversion of hydroxymethylglutaryl-coenzyme A to mevalonic acid catalyzed by the enzyme HMG-CoA reductase. Such inhibition is readily determined by those skilled in the art according to standard assays (e.g., Meth. Enzymol. 1981; 71:455–509, and references cited therein). A variety of these compounds are described and referenced below; however, other HMG-CoA reductase inhibitors will be known to those skilled in the art. U.S. Pat. No. 4,231,938 discloses certain compounds isolated after cultivation of a microorganism belonging to the genus Aspergillus, such as lovastatin. Also, U.S. Pat. No. 4,444,784 discloses synthetic derivatives of the aforementioned compounds, such as simvastatin. Also, U.S. Pat. No. 4,739,073 discloses certain substituted indoles, such as fluvastatin. Also, U.S. Pat. No. 4,346,227 discloses ML-236B derivatives, such as pravastatin. Also, EP-491226A discloses certain pyridyldihydroxyheptenoic acids, such as cerivastatin. In addition, U.S. Pat. No. 5,273,995 discloses certain 6-[2-(substituted-pyrrol-1-yl)alkyl]pyran-2-ones such as atorvastatin and the hemicalcium salt thereof (Lipitor®). Additional HMG-CoA reductase inhibitors include rosuvastatin and pitavastatin.

Any MTP/Apo B secretion (microsomal triglyceride transfer protein and/or apolipoprotein B secretion) inhibitor can be used as the second compound in the combination aspect of the present invention. The term MTP/Apo B secretion inhibitor refers to compounds which inhibit the secretion of triglycerides, cholesteryl ester and phospholipids. Such inhibition is readily determined by those skilled in the art according to standard assays (e.g., Wetterau, J. R. 1992; Science 258:999). A variety of these compounds are known to those skilled in the art, including implitapide (Bayer) and additional compounds such as those disclosed in WO 96/40640 and WO 98/23593.

Any HMG-CoA synthase inhibitor can be used as the second compound in the combination aspect of the present invention. The term HMG-CoA synthase inhibitor refers to compounds which inhibit the biosynthesis of hydroxymethylglutaryl-coenzyme A from acetyl-coenzyme A and acetoacetyl-coenzyme A, catalyzed by the enzyme HMG-CoA synthase. Such inhibition is readily determined by those skilled in the art according to standard assays (e.g., Meth Enzymol. 1975; 35:155–160: Meth. Enzymol. 1985; 110:19–26 and references cited therein). A variety of these compounds are described and referenced below, however other HMG-CoA synthase inhibitors will be known to those skilled in the art. U.S. Pat. No. 5,120,729 discloses certain beta-lactam derivatives. U.S. Pat. No. 5,064,856 discloses certain spiro-lactone derivatives prepared by culturing a microorganism (MF5253). U.S. Pat. No. 4,847,271 discloses certain oxetane compounds such as 11-(3-hydroxymethyl-4-oxo-2-oxetayl)-3,5,7-trimethyl-2,4-undeca-dienoic acid derivatives.

Any compound that decreases HMG-CoA reductase gene expression can be used as the second compound in the combination aspect of the present invention. These agents can be HMG-CoA reductase transcription inhibitors that block or decrease the transcription of DNA or translation inhibitors that prevent or decrease translation of mRNA coding for HMG-CoA reductase into protein. Such compounds may either affect transcription or translation directly, or may be biotransformed to compounds that have the aforementioned activities by one or more enzymes in the cholesterol biosynthetic cascade or may lead to the accumulation of an isoprene metabolite that has the aforementioned activities. Such regulation is readily determined by those skilled in the art according to standard assays (e.g., Meth. Enzymol. 1985; 110:9–19). Inhibitors of HMG-CoA reductase gene expression will be known to those skilled in the art, for example, U.S. Pat. No. 5,041,432 discloses certain 15-substituted lanosterol derivatives. Other oxygenated sterols that suppress synthesis of HMG-CoA reductase are discussed by E. I. Mercer (Prog. Lip. Res. 1993; 32:357–416).

Any compound having activity as a CETP inhibitor can serve as the second compound in the combination therapy aspect of the present invention. The term CETP inhibitor refers to compounds that inhibit the cholesteryl ester transfer protein (CETP) mediated transport of various cholesteryl esters and triglycerides from HDL to LDL and VLDL. Such CETP inhibition activity is readily determined by those skilled in the art according to standard assays (e.g., U.S. Pat. No. 6,140,343). A variety of CETP inhibitors will be known to those skilled in the art, for example, those disclosed in commonly assigned U.S. Pat. No. 6,140,343 and commonly assigned U.S. Pat. No. 6,197,786. CETP inhibitors disclosed in these patents include compounds, such as [2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester, which is also known as torcetrapib. Other CETP inhibitors are disclosed, for example, in U.S. publication 2002/0177708, U.S. publication 2002/0120011, PCT publication WO 0018724, PCT publication WO 0018721, and U.S. provisional application 60/458,274, filed Mar. 28, 2003. U.S. Pat. No. 5,512,548 discloses certain polypeptide derivatives having activity as CETP inhibitors, while certain CETP-inhibitory rosenonolactone derivatives and phosphate-containing analogs of cholesteryl ester are disclosed in *J. Antibiot.*, 49(8): 815–816 (1996), and *Bioorg. Med. Chem. Lett.;* 6:1951–1954 (1996), respectively.

Any squalene synthetase inhibitor can be used as the second compound of the present invention. The term squalene synthetase inhibitor refers to compounds which inhibit the condensation of 2 molecules of farnesylpyrophosphate to form squalene, catalyzed by the enzyme squalene synthetase. Such inhibition is readily determined by those skilled in the art according to standard assays (e.g., Meth. Enzymol. 1969; 15: 393–454 and Meth. Enzymol. 1985; 110:359–373 and references contained therein). A variety of these compounds are known to those skilled in the art, for example, U.S. Pat. No. 5,026,554 discloses fermentation products of the microorganism MF5465 (ATCC 74011) including zaragozic acid. A summary of other squalene synthetase inhibitors has been compiled (see, e.g., Curr. Op. Ther. Patents (1993) 861–4).

Any squalene epoxidase inhibitor can be used as the second compound in the combination aspect of the present invention. The term squalene epoxidase inhibitor refers to compounds which inhibit the bioconversion of squalene and molecular oxygen into squalene-2,3-epoxide, catalyzed by the enzyme squalene epoxidase. Such inhibition is readily determined by those skilled in the art according to standard assays (e.g., Biochim. Biophys. Acta 1984; 794:466–471). A variety of these compounds are known to those skilled in the art, for example, U.S. Pat. Nos. 5,011,859 and 5,064,864 disclose certain fluoro analogs of squalene. EP publication 395,768 A discloses certain substituted allylamine derivatives. PCT publication WO 9312069 A discloses certain amino alcohol derivatives. U.S. Pat. No. 5,051,534 discloses certain cyclopropyloxy-squalene derivatives.

Any squalene cyclase inhibitor can be used as the second component in the combination aspect of the present invention. The term squalene cyclase inhibitor refers to compounds which inhibit the bioconversion of squalene-2,3-epoxide to lanosterol, catalyzed by the enzyme squalene cyclase. Such inhibition is readily determined by those skilled in the art according to standard assays (e.g., FEBS Lett. 1989; 244:347–350). Squalene cyclase inhibitors are known to those skilled in the art. For example, PCT publication WO9410150 and French patent publication 2697250 disclose squalene cyclase inhibitors.

Any combined squalene epoxidase/squalene cyclase inhibitor can be used as the second component in the combination aspect of the present invention. The term combined squalene epoxidase/squalene cyclase inhibitor refers to compounds that inhibit the bioconversion of squalene to lanosterol via a squalene-2,3-epoxide intermediate. In some assays, it is not possible to distinguish between squalene epoxidase inhibitors and squalene cyclase inhibitors. However, these assays are recognized by those skilled in the art. Thus, inhibition by combined squalene epoxidase/squalene cyclase inhibitors is readily determined by those skilled in art according to the aforementioned standard assays for squalene cyclase or squalene epoxidase inhibitors. A variety of squalene epoxidase/squalene cyclase inhibitors are known to those skilled in the art. U.S. Pat. Nos. 5,084,461 and 5,278,171 disclose certain azadecalin derivatives. EP publication 468,434 discloses certain piperidyl ether and thio-ether derivatives such as 2-(1-piperidyl)pentyl isopentyl sulfoxide and 2-(1-piperidyl)ethyl ethyl sulfide. PCT publication WO 9401404 discloses certain acylpiperidines such as 1-(1-oxopentyl-5-phenylthio)-4-(2-hydroxy-1-methyl)ethyl)piperidine. U.S. Pat. No. 5,102,915 discloses certain cyclopropyloxy-squalene derivatives.

Any ACAT inhibitor can serve as the second compound in the combination therapy aspect of the present invention. The term ACAT inhibitor refers to compounds that inhibit the intracellular esterification of dietary cholesterol by the enzyme acyl CoA: cholesterol acyltransferase. Such inhibition may be determined readily by one of skill in the art according to standard assays, such as the method of Heider et al. described in *Journal of Lipid Research.*, 24:1127 (1983). A variety of these compounds are known to those skilled in the art, for example, U.S. Pat. No. 5,510,379 discloses certain carboxysulfonates, while WO 96/26948 and WO 96/10559 both disclose urea derivatives having ACAT inhibitory activity. Examples of ACAT inhibitors include compounds such as Avasimibe (Pfizer), CS-505 (Sankyo) and Eflucimibe (Eli Lilly and Pierre Fabre).

A lipase inhibitor can serve as the second compound in the combination therapy aspect of the present invention. A lipase inhibitor is a compound that inhibits the metabolic cleavage of dietary triglycerides into free fatty acids and monoglycerides. Under normal physiological conditions, lipolysis occurs via a two-step process that involves acylation of an activated serine moiety of the lipase enzyme. This leads to the production of a fatty acid-lipase hemiacetal intermediate, which is then cleaved to release a diglyceride. Following further deacylation, the lipase-fatty acid intermediate is cleaved, resulting in free lipase, a monoglyceride and a fatty acid. The resultant free fatty acids and monoglycerides are incorporated into bile acid-phospholipid micelles, which are subsequently absorbed at the level of the brush border of the small intestine. The micelles eventually enter the peripheral circulation as chylomicrons. Such lipase inhibition activity is readily determined by those skilled in the art according to standard assays (e.g., Methods Enzymol. 286: 190–231).

Pancreatic lipase mediates the metabolic cleavage of fatty acids from triglycerides at the 1- and 3-carbon positions. The primary site of the metabolism of ingested fats is in the duodenum and proximal jejunum by pancreatic lipase, which is usually secreted in vast excess of the amounts necessary for the breakdown of fats in the upper small intestine. Because pancreatic lipase is the primary enzyme required for the absorption of dietary triglycerides, inhibitors have utility in the treatment of obesity and the other related conditions. Such pancreatic lipase inhibition activity is readily determined by those skilled in the art according to standard assays (e.g., Methods Enzymol. 286: 190–231).

Gastric lipase is an immunologically distinct lipase that is responsible for approximately 10 to 40% of the digestion of dietary fats. Gastric lipase is secreted in response to mechanical stimulation, ingestion of food, the presence of a fatty meal or by sympathetic agents. Gastric lipolysis of ingested fats is of physiological importance in the provision of fatty acids needed to trigger pancreatic lipase activity in the intestine and is also of importance for fat absorption in a variety of physiological and pathological conditions associated with pancreatic insufficiency. See, for example, C. K. Abrams, et al., *Gastroenterology,* 92,125 (1987). Such gastric lipase inhibition activity is readily determined by those skilled in the art according to standard assays (e.g., Methods Enzymol. 286: 190–231).

A variety of gastric and/or pancreatic lipase inhibitors are known to one of ordinary skill in the art. Preferred lipase inhibitors are those inhibitors that are selected from the group consisting of lipstatin, tetrahydrolipstatin (orlistat), valilactone, esterastin, ebelactone A, and ebelactone B. The compound tetrahydrolipstatin is especially preferred. The lipase inhibitor, N-3-trifluoromethylphenyl-N'-3-chloro-4'-trifluoromethylphenylurea, and the various urea derivatives related thereto, are disclosed in U.S. Pat. No. 4,405,644. The lipase inhibitor, esteracin, is disclosed in U.S. Pat. Nos. 4,189,438 and 4,242,453. The lipase inhibitor, cyclo-O,O'-[(1,6-hexanediyl)-bis-(iminocarbonyl)]dioxime, and the various bis(iminocarbonyl)dioximes related thereto may be prepared as described in Petersen et al., *Liebig's Annalen,* 562, 205–229 (1949).

A variety of pancreatic lipase inhibitors are described herein below. The pancreatic lipase inhibitors lipstatin, (2S, 3S, 5S, 7Z, 10Z)-5-[(S)-2-formamido-4-methyl-valeryloxy]-2-hexyl-3-hydroxy-7,10-hexadecanoic acid lactone, and tetrahydrolipstatin (orlistat), (2S, 3S, 5S)-5-[(S)-2-formamido-4-methyl-valeryloxy] -2-hexyl-3-hydroxy-hexadecanoic 1,3 acid lactone, and the variously substituted N-formylleucine derivatives and stereoisomers thereof, are disclosed in U.S. Pat. No. 4,598,089. For example, tetrahydrolipstatin is prepared as described in, e.g., U.S. Pat. Nos. 5,274,143; 5,420,305; 5,540,917; and 5,643,874. The pancreatic lipase inhibitor, FL-386, 1-[4-(2-methylpropyl)cyclohexyl]-2-[(phenylsulfonyl)oxy]ethanone, and the variously substituted sulfonate derivatives related thereto, are disclosed in U.S. Pat. No. 4,452,813. The pancreatic lipase inhibitor, WAY-121898, 4-phenoxyphenyl-4-methylpiperidin-1-yl-carboxylate, and the various carbamate esters and pharmaceutically acceptable salts related thereto, are disclosed in U.S. Pat. Nos. 5,512,565; 5,391,571 and 5,602, 151. The pancreatic lipase inhibitor, valilactone, and a process for the preparation thereof by the microbial cultivation of *Actinomycetes* strain MG147-CF2, are disclosed in Kitahara, et al., *J. Antibiotics,* 40 (11), 1647–1650 (1987). The pancreatic lipase inhibitors, ebelactone A and ebelactone B, and a process for the preparation thereof by the microbial cultivation of *Actinomycetes* strain MG7-G1, are disclosed in Umezawa, et al., *J. Antibiotics,* 33, 1594–1596 (1980). The use of ebelactones A and B in the suppression of monoglyceride formation is disclosed in Japanese Kokai 08–143457, published Jun. 4, 1996.

Other compounds that are marketed for hyperlipidemia, including hypercholesterolemia and which are intended to help prevent or treat atherosclerosis include bile acid sequestrants, such as Welchol®, Colestid®, LoCholest® and Questran®; and fibric acid derivatives, such as Atromid®, Lopid® and Tricor®.

Diabetes can be treated by administering to a patient having diabetes (especially Type II), insulin resistance, impaired glucose tolerance, or the like, or any of the diabetic complications such as neuropathy, nephropathy, retinopathy or cataracts, a therapeutically effective amount of a Formula I compound in combination with other agents (e.g., insulin) that can be used to treat diabetes. This includes the classes of anti-diabetic agents (and specific agents) described herein.

Any glycogen phosphorylase inhibitor can be used as the second agent in combination with a Formula I compound of the present invention. The term glycogen phosphorylase inhibitor refers to compounds that inhibit the bioconversion of glycogen to glucose-1-phosphate which is catalyzed by the enzyme glycogen phosphorylase. Such glycogen phosphorylase inhibition activity is readily determined by those skilled in the art according to standard assays (e.g., J. Med. Chem. 41 (1998) 2934–2938). A variety of glycogen phosphorylase inhibitors are known to those skilled in the art including those described in WO 96/39384 and WO 96/39385.

Any aldose reductase inhibitor can be used in combination with a Formula I compound of the present invention. The term aldose reductase inhibitor refers to compounds that inhibit the bioconversion of glucose to sorbitol, which is catalyzed by the enzyme aldose reductase. Aldose reductase inhibition is readily determined by those skilled in the art according to standard assays (e.g., J. Malone, Diabetes, 29:861–864 (1980). "Red Cell Sorbitol, an Indicator of Diabetic Control"). A variety of aldose reductase inhibitors are known to those skilled in the art.

Any sorbitol dehydrogenase inhibitor can be used in combination with a Formula I compound of the present invention. The term sorbitol dehydrogenase inhibitor refers to compounds that inhibit the bioconversion of sorbitol to fructose which is catalyzed by the enzyme sorbitol dehydrogenase. Such sorbitol dehydrogenase inhibitor activity is readily determined by those skilled in the art according to standard assays (e.g., Analyt. Biochem (2000) 280: 329–331). A variety of sorbitol dehydrogenase inhibitors are known, for example, U.S. Pat. Nos. 5,728,704 and 5,866,578 disclose compounds and a method for treating or preventing diabetic complications by inhibiting the enzyme sorbitol dehydrogenase.

Any glucosidase inhibitor can be used in combination with a Formula I compound of the present invention. A glucosidase inhibitor inhibits the enzymatic hydrolysis of complex carbohydrates by glycoside hydrolases, for example amylase or maltase, into bioavailable simple sugars, for example, glucose. The rapid metabolic action of glucosidases, particularly following the intake of high levels of carbohydrates, results in a state of alimentary hyperglycemia which, in adipose or diabetic subjects, leads to enhanced secretion of insulin, increased fat synthesis and a reduction in fat degradation. Following such hyperglycemias, hypoglycemia frequently occurs, due to the augmented levels of insulin present. Additionally, it is known chyme remaining in the stomach promotes the production of gastric juice, which initiates or favors the development of gastritis or duodenal ulcers. Accordingly, glucosidase inhibitors are known to have utility in accelerating the passage of carbohydrates through the stomach and inhibiting the absorption of glucose from the intestine. Furthermore, the conversion of carbohydrates into lipids of the fatty tissue and the subsequent incorporation of alimentary fat into fatty tissue deposits is accordingly reduced or delayed, with the concomitant benefit of reducing or preventing the deleterious abnormalities resulting therefrom. Such glucosidase inhibition activity is readily determined by those skilled in the art according to standard assays (e.g., Biochemistry (1969) δ: 4214).

A generally preferred glucosidase inhibitor includes an amylase inhibitor. An amylase inhibitor is a glucosidase inhibitor that inhibits the enzymatic degradation of starch or glycogen into maltose. Such amylase inhibition activity is readily determined by those skilled in the art according to standard assays (e.g., Methods Enzymol. (1955) 1: 149). The inhibition of such enzymatic degradation is beneficial in reducing amounts of bioavailable sugars, including glucose and maltose, and the concomitant deleterious conditions resulting therefrom.

A variety of glucosidase inhibitors are known to one of ordinary skill in the art and examples are provided below. Preferred glucosidase inhibitors are those inhibitors that are selected from the group consisting of acarbose, adiposine, voglibose, miglitol, emiglitate, camiglibose, tendamistate, trestatin, pradimicin-Q and salbostatin. The glucosidase inhibitor, acarbose, and the various amino sugar derivatives related thereto are disclosed in U.S. Pat. Nos. 4,062,950 and 4,174,439 respectively. The glucosidase inhibitor, adiposine, is disclosed in U.S. Pat. No. 4,254,256. The glucosidase inhibitor, voglibose, 3,4-dideoxy-4-[[2-hydroxy-1-(hydroxymethyl)ethyl]amino]-2-C-(hydroxymethyl)-D-epi-inositol, and the various N-substituted pseudo-aminosugars related thereto, are disclosed in U.S. Pat. No. 4,701,559. The glucosidase inhibitor, miglitol, (2R,3R,4R,5S)-1-(2-hydroxyethyl)-2-(hydroxymethyl)-3,4,5-piperidinetriol, and the various 3,4,5-trihydroxypiperidines related thereto, are disclosed in U.S. Pat. No. 4,639,436. The glucosidase inhibitor, emiglitate, ethyl p-[2-[(2R,3R,4R,5S)-3,4,5-trihydroxy-2-(hydroxymethyl)piperidino]ethoxy]-benzoate, the various derivatives related thereto and pharmaceutically acceptable acid addition salts thereof, are disclosed in U.S. Pat. No. 5,192,772. The glucosidase inhibitor, MDL-25637, 2,6-dideoxy-7-O-β-D-glucopyrano-syl-2,6-imino-D-glycero-L-gluco-heptitol, the various homodisaccharides related thereto and the pharmaceutically acceptable acid addition salts thereof, are disclosed in U.S. Pat. No. 4,634,765. The glucosidase inhibitor, camiglibose, methyl 6-deoxy-6-[(2R, 3R,4R,5S)-3,4,5-trihydroxy-2-(hydroxymethyl)piperidino]-α-D-glucopyranoside sesquihydrate, the deoxy-nojirimycin derivatives related thereto, the various pharmaceutically acceptable salts thereof and synthetic methods for the preparation thereof, are disclosed in U.S. Pat. Nos. 5,157,116 and 5,504,078. The glycosidase inhibitor, salbostatin and the various pseudosaccharides related thereto, are disclosed in U.S. Pat. No. 5,091,524.

A variety of amylase inhibitors are known to one of ordinary skill in the art. The amylase inhibitor, tendamistat and the various cyclic peptides related thereto, are disclosed in U.S. Pat. No. 4,451,455. The amylase inhibitor Al-3688 and the various cyclic polypeptides related thereto are disclosed in U.S. Pat. No. 4,623,714. The amylase inhibitor, trestatin, consisting of a mixture of trestatin A, trestatin B and trestatin C and the various trehalose-containing amino-sugars related thereto are disclosed in U.S. Pat. No. 4,273,765.

Additional anti-diabetic compounds, which can be used as the second agent in combination with a Formula I compound of the present invention, includes, for example, the following: biguanides (e.g., metformin), insulin secretagogues (e.g., sulfonylureas and glinides), glitazones, non-glitazone PPARγ agonists, PPARβ agonists, inhibitors of DPP-IV, inhibitors of PDE5, inhibitors of GSK-3, glucagon antagonists, inhibitors of f-1,6-BPase(Metabasis/Sankyo), GLP-1/analogs (AC 2993, also known as exendin-4), insulin and insulin mimetics (Merck natural products). Other examples would include PKC-β inhibitors and AGE breakers.

The Formula I compounds of the present invention can be used in combination with other anti-obesity agents. Any anti-obesity agent can be used as the second agent in such combinations and examples are provided herein. Such anti-obesity activity is readily determined by those skilled in the art according to standard assays known in the art.

Suitable anti-obesity agents include phenylpropanolamine, ephedrine, pseudoephedrine, phentermine, β$_3$ adrenergic receptor agonists, apolipoprotein-B secretion/microsomal triglyceride transfer protein (apo-B/MTP) inhibitors, MCR-4 agonists, cholecystokinin-A (CCK-A) agonists, monoamine reuptake inhibitors (e.g., sibutramine), sympathomimetic agents, serotoninergic agents, cannabinoid receptor antagonists (e.g., rimonabant (SR-141,716A)), dopamine agonists (e.g., bromocriptine), melanocyte-stimulating hormone receptor analogs, 5HT2c agonists, melanin concentrating hormone antagonists, leptin (the OB protein), leptin analogs, leptin receptor agonists, galanin antagonists, lipase inhibitors (e.g., tetrahydrolipstatin, i.e. orlistat), bombesin agonists, anorectic agents (e.g., a bombesin agonist), Neuropeptide-Y antagonists, thyroxine, thyromimetic agents, dehydroepiandrosterones or analogs thereof, glucocorticoid receptor agonists or antagonists, orexin receptor antagonists, urocortin binding protein antagonists, glucagon-like peptide-1 receptor agonists, ciliary neurotrophic factors (e.g., Axokine™), human agouti-related proteins (AGRP), ghrelin receptor antagonists, histamine 3 receptor antagonists or inverse agonists, neuromedin U receptor agonists, and the like.

Any thyromimetic can be used as the second agent in combination with a Formula I compound of the present invention. Such thyromimetic activity is readily determined by those skilled in the art according to standard assays (e.g., Atherosclerosis (1996) 126: 53–63). A variety of thyromimetic agents are known to those skilled in the art, for example those disclosed in U.S. Pat. Nos. 4,766,121; 4,826,876; 4,910,305; 5,061,798; 5,284,971; 5,401,772; 5,654,468; and 5,569,674. Other antiobesity agents include sibutramine which can be prepared as described in U.S. Pat. No. 4,929,629. and bromocriptine which can be prepared as described in U.S. Pat. Nos. 3,752,814 and 3,752,888.

The Formula I compounds of the present invention can also be used in combination with other antihypertensive agents. Any anti-hypertensive agent can be used as the second agent in such combinations and examples are provided herein. Such antihypertensive activity is readily determined by those skilled in the art according to standard assays (e.g., blood pressure measurements).

Examples of presently marketed products containing antihypertensive agents include calcium channel blockers, such as Cardizem®, Adalat®, Calan®, Cardene®, Covera®, Dilacor®, DynaCirc®, Procardia XL®, Sular®, Tiazac®, Vascor®, Verelan®, Isoptin®, Nimotop®, Norvasc®, and Plendil®; angiotensin converting enzyme (ACE) inhibitors, such as Accupril®, Altace®, Captopril®, Lotensin®, Mavik®, Monopril®, Prinivil®, Univasc®, Vasotec® and Zestril®.

Osteoporosis is a systemic skeletal disease, characterized by low bone mass and deterioration of bone tissue, with a consequent increase in bone fragility and susceptibility to fracture. In the U.S., the condition affects more than 25 million people and causes more than 1.3 million fractures each year, including 500,000 spine, 250,000 hip and 240,000 wrist fractures annually. Hip fractures are the most serious consequence of osteoporosis, with 5–20% of patients dying within one year, and over 50% of survivors being incapacitated.

The elderly are at greatest risk of osteoporosis, and the problem is therefore predicted to increase significantly with the aging of the population. Worldwide fracture incidence is forecasted to increase three-fold over the next 60 years, and one study has estimated that there will be 4.5 million hip fractures worldwide in 2050.

Women are at greater risk of osteoporosis than men. Women experience a sharp acceleration of bone loss during the five years following menopause. Other factors that increase the risk include smoking, alcohol abuse, a sedentary lifestyle and low calcium intake.

Those skilled in the art will recognize that anti-resorptive agents (for example progestins, polyphosphonates, bisphosphonate(s), estrogen agonists/antagonists, estrogen, estrogen/progestin combinations, Premarin®, estrone, estriol or 17α- or 17β-ethynyl estradiol) may be used in conjunction with the compounds of Formula I of the present invention.

Exemplary progestins are available from commercial sources and include: algestone acetophenide, altrenogest, amadinone acetate, anagestone acetate, chlormadinone acetate, cingestol, clogestone acetate, clomegestone acetate, delmadinone acetate, desogestrel, dimethisterone, dydrogesterone, ethynerone, ethynodiol diacetate, etonogestrel, flurogestone acetate, gestaclone, gestodene, gestonorone caproate, gestrinone, haloprogesterone, hydroxyprogesterone caproate, levonorgestrel, lynestrenol, medrogestone, medroxyprogesterone acetate, melengestrol acetate, methynodiol diacetate, norethindrone, norethindrone acetate, norethynodrel, norgestimate, norgestomet, norgestrel, oxogestone phenpropionate, progesterone, quingestanol acetate, quingestrone, and tigestol.

Preferred progestins are medroxyprogestrone, norethindrone and norethynodrel.

Exemplary bone resorption inhibiting polyphosphonates include polyphosphonates of the type disclosed in U.S. Pat. No. 3,683,080, the disclosure of which is incorporated herein by reference. Preferred polyphosphonates are geminal diphosphonates (also referred to as bis-phosphonates). Tiludronate disodium is an especially preferred polyphosphonate. Ibandronic acid is an especially preferred polyphosphonate. Alendronate and resindronate are especially preferred polyphosphonates. Zoledronic acid is an especially preferred polyphosphonate. Other preferred polyphosphonates are 6-amino-1-hydroxy-hexylidene-bisphosphonic acid and 1-hydroxy-3(methylpentylamino)-propylidene-bis-phosphonic acid. The polyphosphonates may be administered in the form of the acid, or of a soluble alkali metal salt or alkaline earth metal salt. Hydrolyzable esters of the polyphosphonates are likewise included. Specific examples include ethane-1-hydroxy 1,1-diphosphonic acid, methane diphosphonic acid, pentane-1-hydroxy-1,1-diphosphonic acid, methane dichloro diphosphonic acid, methane hydroxy diphosphonic acid, ethane-1-amino-1,1-diphosphonic acid, ethane-2-amino-1,1-diphosphonic acid, propane-3-amino-1-hydroxy-1,1-diphosphonic acid, propane-N,N-dimethyl-3-amino-1-hydroxy-1,1-diphosphonic acid, propane-3,3-dimethyl-3-amino-1-hydroxy-1,1-diphosphonic acid, phenyl amino methane diphosphonic acid,N,N-dimethylamino methane diphosphonic acid, N(2-hydroxyethyl) amino methane diphosphonic acid, butane-4-amino-1-hydroxy-1,1-diphosphonic acid, pentane-5-amino-1-hydroxy-1,1-diphosphonic acid, hexane-6-amino-1-hydroxy-1,1-diphosphonic acid and pharmaceutically acceptable esters and salts thereof.

In particular, the compounds of this invention may be combined with a mammalian estrogen agonist/antagonist. Any estrogen agonist/antagonist may be used as the second compound of this invention. The term estrogen agonist/antagonist refers to compounds which bind with the estrogen receptor, inhibit bone turnover and/or prevent bone loss. In particular, estrogen agonists are herein defined as chemical compounds capable of binding to the estrogen receptor sites in mammalian tissue, and mimicking the actions of estrogen in one or more tissue. Estrogen antagonists are herein defined as chemical compounds capable of binding to the estrogen receptor sites in mammalian tissue, and blocking the actions of estrogen in one or more tissues. Such activities are readily determined by those skilled in the art of standard assays including estrogen receptor binding assays, standard bone histomorphometric and densitometer methods, and Eriksen E. F. et al., Bone Histomorphometry, Raven Press, New York, 1994, pages 1–74; Grier S. J. et. al., The Use of Dual-Energy X-Ray Absorptiometry In Animals, Inv. Radiol., 1996, 31(1):50–62; Wahner H. W. and Fogelman I., The Evaluation of Osteoporosis: Dual Energy X-Ray Absorptiometry in Clinical Practice., Martin Dunitz Ltd., London 1994, pages 1–296). A variety of these compounds are described and referenced below.

Another preferred estrogen agonist/antagonist is 3-(4-(1,2-diphenyl-but-1-enyl)-phenyl)-acrylic acid, which is disclosed in Willson et al., Endocrinology, 1997, 138, 3901–3911.

Another preferred estrogen agonist/antagonist is tamoxifen: (ethanamine,2-(-4-(1,2-diphenyl-1-butenyl)phenoxy)-N,N-dimethyl, (Z)-2-, 2-hydroxy-1,2,3-propanetricarboxylate(1:1)) and related compounds which are disclosed in U.S. Pat. No. 4,536,516, the disclosure of which is incorporated herein by reference.

Another related compound is 4-hydroxy tamoxifen, which is disclosed in U.S. Pat. No. 4,623,660, the disclosure of which is incorporated herein by reference.

A preferred estrogen agonist/antagonist is raloxifene: (methanone, (6-hydroxy-2-(4-hydroxyphenyl)benzo[b]thien-3-yl)(4-(2-(1-piperidinyl)ethoxy)phenyl)-hydrochloride) which is disclosed in U.S. Pat. No. 4,418,068, the disclosure of which is incorporated herein by reference.

Another preferred estrogen agonist/antagonist is toremifene: (ethanamine, 2-(4-(4-chloro-1,2-diphenyl-1-butenyl)phenoxy)-N,N-dimethyl-, (Z)—, 2-hydroxy-1,2,3-propanetricarboxylate (1:1) which is disclosed in U.S. Pat. No. 4,996,225, the disclosure of which is incorporated herein by reference.

Another preferred estrogen agonist/antagonist is centchroman: 1-(2-((4-(-methoxy-2,2, dimethyl-3-phenyl-chroman-4-yl)-phenoxy)-ethyl)-pyrrolidine, which is disclosed in U.S. Pat. No. 3,822,287, the disclosure of which is incorporated herein by reference. Also preferred is levormeloxifene.

Another preferred estrogen agonist/antagonist is idoxifene: (E)-1-(2-(4-(1-(4-iodo-phenyl)-2-phenyl-but-1-enyl)-phenoxy)-ethyl)-pyrrolidinone, which is disclosed in U.S. Pat. No. 4,839,155, the disclosure of which is incorporated herein by reference.

Another preferred estrogen agonist/antagonist is 2-(4-methoxy-phenyl)-3-[4-(2-piperidin-1-yl-ethoxy)-phenoxy]-benzo[b]thiophen-6-ol which is disclosed in U.S. Pat. No. 5,488,058, the disclosure of which is incorporated herein by reference.

Another preferred estrogen agonist/antagonist is 6-(4-hydroxy-phenyl)-5-(4-(2-piperidin-1-yl-ethoxy)-benzyl)-naphthalen-2-ol, which is disclosed in U.S. Pat. No. 5,484,795, the disclosure of which is incorporated herein by reference.

Another preferred estrogen agonist/antagonist is (4-(2-(2-aza-bicyclo[ 2.2.1]hept-2-yl)-ethoxy)-phenyl)-(6-hydroxy-2-(4-hydroxy-phenyl)-benzo[ b]thiophen-3-yl)-methanone which is disclosed, along with methods of preparation, in PCT publication no. WO 95/10513 assigned to Pfizer Inc.

Other preferred estrogen agonist/antagonists include the compounds, TSE-424 (Wyeth-Ayerst Laboratories) and arazoxifene.

Other preferred estrogen agonist/antagonists include compounds as described in commonly assigned U.S. Pat. No. 5,552,412, the disclosure of which is incorporated herein by reference. Especially preferred compounds described therein are:

cis-6-(4-fluoro-phenyl)-5-(4-(2-piperidin-1-yl-ethoxy)-phenyl)-5,6,7,8-tetrahydro-naphthalene-2-ol;
(−)-cis-6-phenyl-5-(4-(2-pyrrolidin-1-yl-ethoxy)-phenyl)-5,6,7,8-tetrahydro-naphthalene-2-ol (also known as lasofoxifene);
cis-6-phenyl-5-(4-(2-pyrrolidin-1-yl-ethoxy)-phenyl)-5,6,7,8-tetrahydro-naphthalene-2-ol;
cis-1-(6'-pyrrolodinoethoxy-3'-pyridyl)-2-phenyl-6-hydroxy-1,2,3,4-tetrahydronaphthalene;
1-(4'-pyrrolidinoethoxyphenyl)-2-(4"-fluorophenyl)-6-hydroxy-1,2,3,4-tetrahydroisoquinoline;
cis-6-(4-hydroxyphenyl)-5-(4-(2-piperidin-1-yl-ethoxy)-phenyl)-5,6,7,8-tetrahydro-naphthalene-2-ol; and
1-(4'-pyrrolidinolethoxyphenyl)-2-phenyl-6-hydroxy-1,2,3,4-tetrahydroisoquinoline.

Other estrogen agonist/antagonists are described in U.S. Pat. No. 4,133,814 (the disclosure of which is incorporated herein by reference). U.S. Pat. No. 4,133,814 discloses derivatives of 2-phenyl-3-aroyl-benzothiophene and 2-phenyl-3-aroylbenzothiophene-1-oxide.

Other anti-osteoporosis agents, which can be used as the second agent in combination with a Formula I compound of the present invention, include, for example, the following: parathyroid hormone (PTH) (a bone anabolic agent); parathyroid hormone (PTH) secretagogues (see, e.g., U.S. Pat. No. 6,132,774), particularly calcium receptor antagonists; calcitonin; and vitamin D and vitamin D analogs.

Any selective androgen receptor modulator (SARM) can be used in combination with a Formula I compound of the present invention. A selective androgen receptor modulator (SARM) is a compound that possesses androgenic activity and which exerts tissue-selective effects. SARM compounds can function as androgen receptor agonists, partial agonists, partial antagonists or antagonists. Examples of suitable SARMs include compounds such as cyproterone acetate, chlormadinone, flutamide, hydroxyflutamide, bicalutamide, nilutamide, spironolactone, 4-(trifluoromethyl)-2(1H)-pyrrolidino[3,2-g]quinoline derivatives, 1,2-dihydropyridino[5,6-g]quinoline derivatives and piperidino[3,2-g]quinolinone derivatives.

Cyproterone, also known as (1b,2b)-6-chloro-1,2-dihydro-17-hydroxy-3'H-cyclopropa[ 1,2]pregna-1,4,6-triene-3,20-dione is disclosed in U.S. Pat. No. 3,234,093. Chlormadinone, also known as 17-(acetyloxy)-6-chloropregna-4,6-diene-3,20-dione, in its acetate form, acts as an antiandrogen and is disclosed in U.S. Pat. No. 3,485,852. Nilutamide, also known as 5,5-dimethyl-3-[4-nitro-3-(trifluoromethyl)phenyl]-2,4-imidazolidinedione and by the trade name Nilandron® is disclosed in U.S. Pat. No. 4,097,578. Flutamide, also known as 2-methyl-N-[4-nitro-3-(trifluoromethyl)phenyl]propanamide and the trade name Eulexin® is disclosed in U.S. Pat. No. 3,847,988. Bicalutamide, also known as 4'-cyano-a',a',a'-trifluoro-3-(4-fluorophenylsulfonyl)-2-hydroxy-2-methylpropiono-m-toluidide and the trade name Casodex® is disclosed in EP-100172. The enantiomers of biclutamide are discussed by Tucker and Chesterton, *J. Med. Chem.* 1988, 31, 885–887. Hydroxyflutamide, a known androgen receptor antagonist in most tissues, has been suggested to function as a SARM for effects on IL-6 production by osteoblasts as disclosed in Hofbauer et al. *J. Bone Miner.* Res. 1999, 14, 1330–1337. Additional SARMs have been disclosed in U.S. Pat. No. 6,017,924; WO 01/16108, WO 01/16133, WO 01/16139, WO 02/00617, WO 02/16310, U.S. Patent Application Publication No. U.S. 2002/0099096, U.S. Patent Application Publication No. U.S. 2003/0022868, WO 03/011302 and WO 03/011824. All of the above refences are hereby incorporated by reference herein.

The starting materials and reagents for the above described Formula I compounds of the present invention and combination agents, are also readily available or can be easily synthesized by those skilled in the art using conventional methods of organic synthesis. For example, many of the compounds used herein, are related to, or are derived from compounds in which there is a large scientific interest and commercial need, and accordingly many such compounds are commercially available or are reported in the literature or are easily prepared from other commonly available substances by methods which are reported in the literature.

Some of the Formula I compounds of the present invention or intermediates in their synthesis have asymmetric carbon atoms and therefore are enantiomers or diastereomers. Diasteromeric mixtures can be separated into their individual diastereomers on the basis of their physical chemical differences by methods known per se., for example, by chromatography and/or fractional crystallization. Enantiomers can be separated by, for example, chiral HPLC methods or converting the enantiomeric mixture into a diasteromeric mixture by reaction with an appropriate optically active compound (e.g., alcohol), separating the diastereomers and converting (e.g., hydrolyzing) the individual diastereomers to the corresponding pure enantiomers. Also, an enantiomeric mixture of the Formula I compounds or an intermediate in their synthesis which contain an acidic or basic moiety may be separated into their compounding pure enantiomers by forming a diastereomeric salt with an optically pure chiral base or acid (e.g., 1-phenyl-ethyl amine or tartaric acid) and separating the diasteromers by fractional crystallization followed by neutralization to break the salt, thus providing the corresponding pure enantiomers. All such isomers, including diastereomers, enantiomers and mixtures thereof are considered as part of the present invention. Also, some of the compounds of the present invention are atropisomers (e.g., substituted biaryls) and are considered as part of the present invention.

More specifically, the Formula I compounds of the present invention can be obtained by fractional crystallization of the basic intermediate with an optically pure chiral acid to form a diastereomeric salt. Neutralization techniques are used to remove the salt and provide the enantiomerically pure compounds. Alternatively, the Formula I compounds of the present invention may be obtained in enantiomerically enriched form by resolving the racemate of the final compound or an intermediate in its synthesis (preferably the final compound) employing chromatography (preferably high pressure liquid chromatography [HPLC]) on an asymmetric resin (preferably Chiralcel™ AD or OD (obtained from Chiral Technologies, Exton, Pa.)) with a mobile phase consisting of a hydrocarbon (preferably heptane or hexane) containing between 0 and 50% isopropanol (preferably between 2 and 20%) and between 0 and 5% of an alkyl amine (preferably 0.1% of diethylamine). Concentration of the product containing fractions affords the desired materials.

Some of the Formula I compounds of the present invention are acidic and they form a salt with a pharmaceutically acceptable cation. Some of the Formula I compounds of the present invention are basic and they form a salt with a pharmaceutically acceptable anion. All such salts are within the scope of the present invention and they can be prepared by conventional methods such as combining the acidic and basic entities, usually in a stoichiometric ratio, in either an aqueous, nonaqueous or partially aqueous medium, as appropriate. The salts are recovered either by filtration, by precipitation with a non-solvent followed by filtration, by evaporation of the solvent, or, in the case of aqueous solutions, by lyophilization, as appropriate.

The compounds can be obtained in crystalline form by dissolution in an appropriate solvent(s) such as ethanol, hexanes or water/ethanol mixtures.

Those skilled in the art will recognize that some of the compounds herein can exist in several tautomeric forms. All such tautomeric forms are considered as part of the present invention. For example all enol-keto forms of the compounds of Formula I of the present invention are included in this invention.

In addition, when the Formula I compounds of the present invention form hydrates or solvates they are also within the scope of the present invention.

The Formula I compounds of the present invention, their prodrugs and the salts of such compounds and prodrugs are all adapted to therapeutic use as agents that activate peroxisome proliferator activator receptor (PPAR) activity in mammals, particularly humans. Thus, it is believed the compounds of the present invention, by activating the PPAR receptor, stimulate transcription of key genes involved in fatty acid oxidation and also those involved in high density lipoprotein (HDL) assembly (for example apolipoprotein Al gene transcription), accordingly reducing whole body fat and increasing HDL cholesterol. By virtue of their activity, these agents also reduce plasma levels of triglycerides, VLDL cholesterol, LDL cholesterol and their associated components in mammals, particularly humans, as well as increasing HDL cholesterol and apolipoprotein Al. Hence, these compounds are useful for the treatment and correction of the various dyslipidemias observed to be associated with the development and incidence of atherosclerosis and cardiovascular disease, including hypoalphalipoproteinemia and hypertriglyceridemia.

Given the positive correlation between triglycerides, LDL cholesterol, and their associated apolipoproteins in blood with the development of cardiovascular, cerebral vascular and peripheral vascular diseases, the Formula I compounds of the present invention, their prodrugs and the salts of such compounds and prodrugs, by virtue of their pharmacologic action, are useful for the prevention, arrestment and/or regression of atherosclerosis and its associated disease states. These include cardiovascular disorders (e.g., angina, cardiac ischemia and myocardial infarction) and complications due to cardiovascular disease.

Thus, given the ability of the Formula I compounds of the present invention, their prodrugs and the salts of such compounds and prodrugs to reduce plasma triglycerides and total plasma cholesterol, and increase plasma HDL cholesterol, they are of use in the treatment of diabetes, including impaired glucose tolerance, diabetic complications, insulin resistance and metabolic syndrome, as described previously. In addition, the Formula I compounds are useful for the treatment of polycystic ovary syndrome. Also, the Formula I compounds are useful in the treatment of obesity given the ability of the Formula I compounds of this invention, their prodrugs and the salts of such compounds and prodrugs to increase hepatic fatty acid oxidation.

The utility of the Formula I compounds of the present invention, their prodrugs and the salts of such compounds and prodrugs as medical agents in the treatment of the above described disease/conditions in mammals (e.g. humans, male or female) is demonstrated by the activity of the compounds of the present invention in one or more of the conventional assays and in vivo assays described below. The in vivo assays (with appropriate modifications within the skill in the art) can be used to determine the activity of other lipid or triglyceride controlling agents as well as the compounds of the present invention. Thus, the protocols described below can also be used to demonstrate the utility of the combinations of the agents (i.e., the compounds of the present invention) described herein. In addition, such assays provide a means whereby the activities of the Formula I compounds of the present invention, their prodrugs and the salts of such compounds and prodrugs (or the other agents described herein) can be compared to each other and with the activities of other known compounds. The results of these comparisons are useful for determining dosage levels in mammals, including humans, for the treatment of such diseases. The following protocols can of course be varied by those skilled in the art.

PPAR FRET Assay

Measurement of coactivator recruitment by a nuclear receptor after receptor-ligand association is a method for evaluating the ability of a ligand to produce a functional response through a nuclear receptor. The PPAR FRET (Fluorescence Resonance Energy Transfer) assay measures the ligand-dependent interaction between nuclear receptor and coactivator. GST/PPAR ($\alpha,\beta$, and $\gamma$) ligand binding domain (LBD) is labeled with a europium-tagged anti-GST antibody, while an SRC-1 (Sterol Receptor Coactivator-1) synthetic peptide containing an amino terminus long chain biotin molecule is labeled with streptavidin-linked allophycocyanin (APC). Binding of ligand to the PPAR LBD causes a conformational change that allows SRC-1 to bind. Upon SRC-1 binding, the donor FRET molecule (europium) comes in close proximity to the acceptor molecule (APC), resulting in fluorescence energy transfer between donor (337 nm excitation and 620 nm emission) and acceptor (620 nm excitation and 665 nm emission). Increases in the ratio of 665 nm emission to 620 nm emission is a measure of the ability of the ligand-PPAR LBD to recruit SRC-1 synthetic peptide and therefore a measure of the ability of a ligand to produce a functional response through the PPAR receptor.

[1] GST/PPAR LBD Expression. The human PPARα LBD (amino acids 235507) is fused to the carboxy terminus of glutathione S-transferase (GST) in pGEX-6P-1 (Pharmacia, Piscataway, N.J.). The GST/PPARα LBD fusion protein is expressed in BL21[DE3]pLysS cells using a 50 uM IPTG induction at room temperature for 16 hr (cells induced at an $A_{600}$ of ~0.6). Fusion protein is purified on glutathione sepharose 4B beads, eluted in 10 mM reduced glutathione, and dialyzed against 1×PBS at 4° C. Fusion protein is quantitated by Bradford assay (M. M. Bradford, Analst. Biochem. 72:248–254; 1976), and stored at −20° C. in 1×PBS containing 40% glycerol and 5 mM DTT.

[2] FRET Assay. The FRET assay reaction mix consists of 1× FRET buffer (50 mM Tris-Cl pH 8.0, 50 mM KCl, 0.1 mg/ml BSA, 1 mM EDTA, and 2 mM DTT) containing 20 nM GST/PPARα LBD, 40 nM of SRC-1 peptide (amino acids 676-700, 5'-long chain biotin-CPSSHSSLTERHKILHRLLQEGSPS—$NH_2$, purchased from American Peptide Co., Sunnyvale, Calif.), 2 nM of europium-conjugated anti-GST antibody (Wallac, Gaithersburg, Md.), 40 nM of streptavidin-conjugated APC (Wallac), and control and test compounds. The final volume is brought to 100 ul with water and transferred to a black 96-well plate (Microfuor B, Dynex (Chantilly, Va.)). The reaction mixes are incubated for 1 hr at 4° C. and fluorescence is read in Victor 2 plate reader (Wallac). Data is presented as a ratio of the emission at 665 nm to the emission at 615 nm.

Assessment of Lipid-Modulating Activity in Mice

[1] Triglyceride lowering. The hypolipidemic treating activity of the compounds of the present invention can be demonstrated by methods based on standard procedures. For example, the in vivo activity of these compounds in decreasing plasma triglyceride levels may be determined in hybrid B6CBAF1/J mice.

Male B6CVAF1/J mice (8–11 week old) are obtained from The Jackson Laboratory and housed 4–5/cage and maintained in a 12 hr light/12 hr dark cycle. Animals have ad lib. access to Purina rodent chow and water. The animals are dosed daily (9 AM) by oral gavage with vehicle (water or 0.5% methyl cellulose 0.05% Tween 80) or with vehicle containing test compound at the desired concentration. Plasma triglycerides levels are determined 24 hours after the administration of the last dose (day 3) from blood collected retro-orbitally with heparinized hematocrit tubes. Triglyceride determinations are performed using a commercially available Triglyceride E kit from Wako (Osaka, Japan).

[2] HDL cholesterol elevation. The activity of the compounds of the present invention for raising the plasma level of high density lipoprotein (HDL) in a mammal can be demonstrated in transgenic mice expressing the human apoAl and CETP transgenes (HuAlCETPTg). The transgenic mice for use in this study are described previously in Walsh et al., J. Lipid Res. 1993, 34: 617–623, Agellon et al., J. Biol. Chem. 1991, 266: 10796–10801. Mice expressing the human apoAl and CETP transgenes are obtained by mating transgenic mice expressing the human apoAl transgene (HuAlTg) with CETP mice (HuCETPTg).

Male HuAlCETPTg mice (8–11 week old) are grouped according to their human apo Al levels and have free access to Purina rodent chow and water. Animals are dosed daily by oral gavage with vehicle (water or 0.5% methylcellulose 0.05% Tween 80) or with vehicle containing test compound at the desired dosed for 5 days. HDL-cholesterol and human apoAl are determined initially (day 0) and 90 minutes post dose (day 5) using methods based on standard procedures. Mouse HDL is separated from apoB-containing lipoproteins by dextran sulfate precipitation as described elsewhere (Francone et al., *J. Lipid. Res.* 1996, 37:1268–1277). Cholesterol is measured enzymatically using a commercially available cholesterol/HP Reagent kit (Boehringer MannHeim, Indianapolis, Ind.) and spectrophotometrically quantitated on a microplate reader. Human apoAl is measured by a sandwich enzyme-linked immunosorbent assay as previously described (Francone et al., *J. Lipid. Res.* 1996, 37:1268–1277).

Measurement of Glucose Lowering in the ob/ob Mouse

The hypoglycemic activity of the compounds of the present invention can be determined by the amount of test compound that reduces glucose levels relative to a vehicle without test compound in male ob/ob mice. The test also allows the determination of an approximate minimal effective dose (MED) value for the in vivo reduction of plasma glucose concentration in such mice for such test compounds.

Five to eight week old male C57BL/6J-ob/ob mice (obtained from Jackson Laboratory, Bar Harbor, Me.) are housed five per cage under standard animal care practices. After a one-week acclimation period, the animals are weighed and 25 microliters of blood are collected from the retro-orbital sinus prior to any treatment. The blood sample is immediately diluted 1:5 with saline containing 0.025% sodium heparin, and held on ice for metabolite analysis. Animals are assigned to treatment groups so that each group has a similar mean for plasma glucose concentration. After group assignment, animals are dosed orally each day for four days with the vehicle consisting of either: (1) 0.25% w/v methyl cellulose in water without pH adjustment; or (2) 0.1% Pluronic® P105 Block Copolymer Surfactant (BASF Corporation, Parsippany, N.J.) in 0.1% saline without pH adjustment. On day 5, the animals are weighed again and then dosed orally with a test compound or the vehicle alone. All compounds are administered in vehicle consisting of either: (1) 0.25% w/v methyl cellulose in water; (2) 10% DMSO/0.1% Pluronic® in 0.1% saline without pH adjustment; or 3) neat PEG 400 without pH adjustment. The animals are then bled from the retro-orbital sinus three hours later for determination of blood metabolite levels. The freshly collected samples are centrifuged for two minutes at 10,000×g at room temperature. The supernatant is analyzed for glucose, for example, by the Abbott VP™ (Abbott Laboratories, Diagnostics Division, Irving, Tex.) and VP Super System® Autoanalyzer (Abbott Laboratories, Irving, Tex.), or by the Abbott Spectrum CCX™ (Abbott Laboratories, Irving, Tex.) using the A-Gent™ Glucose-UV Test reagent system (Abbott Laboratories, Irving, Tex.) (a modification of the method of Richterich and Dauwalder, *Schweizerische Medizinische Wochenschrift*, 101: 860 (1971)) (hexokinase method) using a 100 mg/dl standard. Plasma glucose is then calculated by the equation: Plasma glucose (mg/dl)=Sample value×8.14 where 8.14 is the dilution factor, adjusted for plasma hematocrit (assuming the hematocrit is 44%).

The animals dosed with vehicle maintain substantially unchanged hyperglycemic glucose levels (e.g., greater than or equal to 250 mg/dl), animals treated with compounds having hypoglycemic activity at suitable doses have significantly depressed glucose levels. Hypoglycemic activity of the test compounds is determined by statistical analysis (unpaired t-test) of the mean plasma glucose concentration between the test compound group and vehicle-treated group on day 5. The above assay carried out with a range of doses of a test compound allows the determination of an approximate minimal effective dose (MED) value for the in vivo reduction of plasma glucose concentration.

Measurement of Insulin, Triglyceride, and Cholesterol Levels in the ob/ob Mouse

The compounds of the present invention are readily adapted to clinical use as hyperinsulinemia reversing agents, triglyceride lowering agents and hypocholesterolemic agents. Such activity can be determined by the amount of test compound that reduces insulin, triglycerides or cholesterol levels relative to a control vehicle without test compound in male ob/ob mice.

Since the concentration of cholesterol in blood is closely related to the development of cardiovascular, cerebral vascular or peripheral vascular disorders, the compounds of the present invention, by virtue of their hypocholesterolemic action, prevent, arrest and/or regress atherosclerosis.

Since the concentration of insulin in blood is related to the promotion of vascular cell growth and increased renal sodium retention, (in addition to the other actions, e.g., promotion of glucose utilization) and these functions are known causes of hypertension, the compounds of the present invention, by virtue of their hypoinsulinemic action, prevent, arrest and/or regress hypertension.

Since the concentration of triglycerides in blood contributes to the overall levels of blood lipids, the compounds of the present invention, by virtue of their triglyceride lowering and/or free fatty acid lowering activity prevent, arrest and/or regress hyperlipidemia.

Free fatty acids contribute to the overall level of blood lipids and independently have been negatively correlated with insulin sensitivity in a variety of physiologic and pathologic states.

Five to eight week old male C57BL/6J-ob/ob mice (obtained from Jackson Laboratory, Bar Harbor, Me.) are housed five per cage under standard animal care practices and fed standard rodent diet ad libitum. After a one-week acclimation period, the animals are weighed and 25 microliters of blood are collected from the retro-orbital sinus prior to any treatment. The blood sample is immediately diluted 1:5 with saline containing 0.025% sodium heparin, and held on ice for plasma glucose analysis. Animals are assigned to treatment groups so that each group has a similar mean for plasma glucose concentration. The compound to be tested is administered by oral gavage as an about 0.02% to 2.0% solution (weight/volume (w/v)) in either (1) 10% DMSO/0.1% Pluronic® P105 Block Copolymer Surfactant (BASF Corporation, Parsippany, N.J.) in 0.1% saline without pH adjustment or (2) 0.25% w/v methylcellulose in water without pH adjustment. Alternatively, the compound to be tested can be administered by oral gavage dissolved in or in suspension in neat PEG 400. Single daily dosing (s.i.d.) or twice daily dosing (b.i.d.) is maintained for 1 to, for example, 15 days. Control mice receive the 10% DMSO/0.1% Pluronic® P105 in 0.1% saline without pH adjustment or the 0.25% w/v methylcellulose in water without pH adjustment, or the neat PEG 400 without pH adjustment.

Three hours after the last dose is administered, the animals are sacrificed and blood is collected into 0.5 ml serum separator tubes containing 3.6 mg of a 1:1 weight/weight sodium fluoride: potassium oxalate mixture. The freshly collected samples are centrifuged for two minutes at 10,000×g at room temperature, and the serum supernatant is transferred and diluted 1:1 volume/volume with a 1 TIU/ml aprotinin solution in 0.1% saline without pH adjustment.

The diluted serum samples are then stored at −80° C. until analysis. The thawed, diluted serum samples are analyzed for insulin, triglycerides, free fatty acids and cholesterol levels. Serum insulin concentration is determined using Equate® RIA INSULIN kits (double antibody method; as specified by the manufacturer) available from Binax, South Portland, Me. The interassay coefficient of variation is <10%. Serum triglycerides are determined using the Abbott VP™ and VP Super System® Autoanalyzer (Abbott Laboratories, Irving, Tex.), or the Abbott Spectrum CCX™ (Abbott Laboratories, Irving, Tex.) using the A-Gent™ Triglycerides Test reagent system (Abbott Laboratories, Diagnostics Division, Irving, Tex.) (lipase-coupled enzyme method; a modification of the method of Sampson, et al., *Clinical Chemistry* 21: 1983 (1975)). Serum total cholesterol levels are determined using the Abbott VP™ and VP Super System® Autoanalyzer (Abbott Laboratories, Irving, Tex.), and A-Gent™ Cholesterol Test reagent system (cholesterol esterase-coupled enzyme method; a modification of the method of Allain, et al. *Clinical Chemistry* 20: 470 (1974)) using 100 and 300 mg/dl standards. Serum free fatty acid concentration is determined utilizing a kit from WAKO (Osaka, Japan), as adapted for use with the Abbott VP™ and VP Super System® Autoanalyzer (Abbott Laboratories, Irving, Tex.), or the Abbott Spectrum CCX™ (Abbott Laboratories, Irving, Tex.). Serum insulin, triglycerides, free fatty acids and total cholesterol levels are then calculated by the equations: Serum insulin ($\mu$U/ml)=Sample value×2; Serum triglycerides (mg/dl)=Sample value×2; Serum total cholesterol (mg/dl)=Sample value×2; Serum free fatty acid ($\mu$Eq/l)= Sample value×2; where 2 is the dilution factor.

The animals dosed with vehicle maintain substantially unchanged, elevated serum insulin (e.g., 275 $\mu$U/ml), serum triglycerides (e.g., 235 mg/dl), serum free fatty acid (1500 mEq/ml) and serum total cholesterol (e.g., 190 mg/dl) levels. The serum insulin, triglycerides, free fatty acid and total cholesterol lowering activity of the test compounds are determined by statistical analysis (unpaired t-test) of the mean serum insulin, triglycerides, or total cholesterol concentration between the test compound group and the vehicle-treated control group.

Measurement of Energy Expenditure in Rats

As would be appreciated by those skilled in the relevant art, during increased energy expenditure, animals generally consume more oxygen. In addition, metabolic fuels such as, for example, glucose and fatty acids, are oxidized to $CO_2$ and $H_2O$ with the concomitant evolution of heat, commonly referred to in the art as thermogenesis. Thus, the measurement of oxygen consumption in animals, including humans and companion animals, is an indirect measure of thermogenesis. Indirect calorimetry is commonly used in animals, e.g., humans, by those skilled in the relevant art to measure such energy expenditures.

Those skilled in the art understand that increased energy expenditure and the concomitant burning of metabolic fuels resulting in the production of heat may be efficacious with respect to the treatment of, e.g., obesity.

The ability of the Formula I compounds of the present invention to generate a thermogenic response can be demonstrated according to the following protocol: This in vivo screen is designed to evaluate the efficacy of compounds that are PPAR agonists, using as an efficacy endpoint measurement of whole body oxygen consumption. The protocol involves: (a) dosing fatty Zucker rats for about 6 days, and (b) measuring oxygen consumption. Male fatty Zucker rats having a body weight range of from about 400 g to about 500 g are housed for from about 3 to about 7 days in individual cages under standard laboratory conditions prior to the initiation of the study. A compound of the present invention and a vehicle is administered by oral gavage as a single daily dose given between about 3 p.m. to about 6 p.m. for about 6 days. A compound of the present invention is dissolved in vehicle containing about 0.25% of methyl cellulose. The dosing volume is about 1 ml.

About 1 day after the last dose of the compound is administered, oxygen consumption is measured using an open circuit, indirect calorimeter (Oxymax, Columbus Instruments, Columbus, Ohio 43204). The Oxymax gas sensors are calibrated with $N_2$ gas and a gas mixture (about 0.5% of $CO_2$, about 20.5% of $O_2$, about 79% of $N_2$) before each experiment. The subject rats are removed from their home cages and their body weights recorded. The rats are placed into the sealed chambers (43×43×10 cm) of the Oxymax, the chambers are placed in the activity monitors, and the air flow rate through the chambers is then set at from about 1.6 L/min to about 1.7 L/min. The Oxymax software then calculates the oxygen consumption (mL/kg/h) by the rats based on the flow rate of air through the chambers and the difference in oxygen content at the inlet and output ports. The activity monitors have 15 infrared light beams spaced about one inch apart on each axis, and ambulatory activity is recorded when two consecutive beams are broken, and the results are recorded as counts.

Oxygen consumption and ambulatory activity are measured about every 10 min for from about 5 h to about 6.5 h. Resting oxygen consumption is calculated on individual rats by averaging the values excluding the first 5 values and the values obtained during time periods where ambulatory activity exceeds about 100 counts.

In Vivo Atherosclerosis Assay

Anti-atherosclerotic effects of the compounds of the present invention can be determined by the amount of compound required to reduce the lipid deposition in rabbit aorta. Male New Zealand White rabbits are fed a diet containing 0.2% cholesterol and 10% coconut oil for 4 days (meal-fed once per day). Rabbits are bled from the marginal ear vein and total plasma cholesterol values are determined from these samples. The rabbits are then assigned to treatment groups so that each group has a similar mean±SD for total plasma cholesterol concentration, HDL cholesterol concentration and triglyceride concentration. After group assignment, rabbits are dosed daily with compound given as a dietary admix or on a small piece of gelatin based confection. Control rabbits receive only the dosing vehicle, be it the food or the gelatin confection. The cholesterol/coconut oil diet is continued along with the compound administration throughout the study. Plasma cholesterol, HDL-cholesterol, LDL cholesterol and triglyceride values can be determined at any point during the study by obtaining blood from the marginal ear vein. After 3–5 months, the rabbits are sacrificed and the aortae are removed from the thoracic arch to the branch of the iliac arteries. The aortae are cleaned of adventitia, opened longitudinally and then stained with Sudan IV as described by Holman et. al. (Lab. Invest. 1958, 7, 42–47). The percent of the surface area stained is quantitated by densitometry using an Optimas Image Analyzing System (Image Processing Solutions; North Reading Mass.). Reduced lipid deposition is indicated by a reduction in the percent surface area stained in the compound-receiving group in comparison with the control rabbits.

Administration of the compounds of the present invention can be via any method which delivers a compound of this invention systemically and/or locally. These methods include oral routes, parenteral, intraduodenal routes, etc. Generally, the compounds of this invention are administered orally, but parenteral administration (e.g., intravenous, intramuscular, subcutaneous or intramedullary) may be utilized, for example, where oral administration is inappropriate or where the patient is unable to ingest the drug.

In general an amount of a compound of the present invention is used that is sufficient to achieve the therapeutic effect desired (e.g., lipid lowering).

In general an effective dosage for the Formula I compounds of the present invention, their prodrugs and the salts of such compounds and prodrugs is in the range of about 0.001 to about 100 mg/kg/day, preferably about 0.005 to about 5 mg/kg/day.

A dosage of the combination pharmaceutical agents to be used in conjuction with the PPAR agonists is used that is effective for the indication being treated. Such dosages can be determined by standard assays such as those referenced above and provided herein. The combination agents may be administered simultaneously or sequentially in any order.

For example, typically an effective dosage for HMG-CoA reductase inhibitors is in the range of about 0.01 to about 100 mg/kg/day.

The compounds of the present invention are generally administered in the form of a pharmaceutical composition comprising at least one of the compounds of this invention together with a pharmaceutically acceptable vehicle, diluent or carrier. Thus, the compounds of the present invention can be administered individually or together in any conventional oral, parenteral, rectal or transdermal dosage form.

For oral administration a pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. A preferred formulation is a solution or suspension in an oil, for example olive oil, Miglyol™ or Capmul™, in a soft gelatin capsule. Antioxidants may be added to prevent long term degradation as appropriate. When aqueous suspensions and/or elixirs are desired for oral administration, the compounds of the present invention can be combined with various sweetening agents, flavoring agents, coloring agents, emulsifying agents and/or suspending agents, as well as such diluents as water, ethanol, propylene glycol, glycerin and various like combinations thereof.

For purposes of parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well known to those skilled in the art.

For purposes of transdermal (e.g., topical) administration, dilute sterile, aqueous or partially aqueous solutions (usually in about 0.1% to 5% concentration), otherwise similar to the above parenteral solutions, are prepared.

Methods of preparing various pharmaceutical compositions with a certain amount of active ingredient are known, or will be apparent in light of this disclosure, to those skilled in this art. For examples of methods of preparing pharmaceutical compositions, see *Remington's Pharmaceutical Sciences*, Mack Publishing Company, Easter, Pa., 19th Edition (1995).

Pharmaceutical compositions according to the present invention may contain 0.1%–95% of the compound(s) of the present invention, preferably 1%–70%. In any event, the composition or formulation to be administered will contain a quantity of a compound(s) according to the present invention in an amount effective to treat the disease/condition of the subject being treated, e.g., atherosclerosis.

Since the present invention has an aspect that relates to the treatment of the disease/conditions described herein with a combination of active ingredients, which may be administered separately, the invention also relates to combining separate pharmaceutical compositions in kit form. The kit comprises two separate pharmaceutical compositions: a compound of Formula I of the present invention, a prodrug thereof or a salt of such compound or prodrugs and a second compound as described above. The kit comprises means for containing the separate compositions such as a container, a divided bottle or a divided foil packet. Typically the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc . . . Second Week, Monday, Tuesday, . . . " etc. Other variations of memory aids will be readily apparent. A "daily dose" can be a single tablet or capsule or several pills or capsules to be taken on a given day. Also, a daily dose of a compound of the present invention can consist of one tablet or capsule while a daily dose of the second compound can consist of several tablets or capsules and vice versa. The memory aid should reflect this.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The compounds of the present invention either alone or in combination with each other or other compounds generally will be administered in a convenient formulation. The following formulation examples only are illustrative and are not intended to limit the scope of the present invention.

In the formulations which follow, "active ingredient" means a compound of the present invention.

Formulation 1: Gelatin Capsules
Hard gelatin capsules are prepared using the following:

| Ingredient | Quantity (mg/capsule) |
|---|---|
| Active ingredient | 0.25–100 |
| Starch, NF | 0–650 |
| Starch flowable powder | 0–50 |
| Silicone fluid 350 centistokes | 0–15 |

A tablet formulation is prepared using the ingredients below:

Formulation 2: Tablets

| Ingredient | Quantity (mg/tablet) |
|---|---|
| Active ingredient | 0.25–100 |
| Cellulose, microcrystalline | 200–650 |
| Silicon dioxide, fumed | 10–650 |
| Stearate acid | 5–15 |

The components are blended and compressed to form tablets.

Alternatively, tablets each containing 0.25–100 mg of active ingredients are made up as follows:

Formulation 3: Tablets

| Ingredient | Quantity (mg/tablet) |
|---|---|
| Active ingredient | 0.25–100 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredients, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.25–100 mg of active ingredient per 5 ml dose are made as follows:

Formulation 4: Suspensions

| Ingredient | Quantity (mg/5 ml) |
|---|---|
| Active ingredient | 0.25–100 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified Water to | 5 mL |

The active ingredient is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

An aerosol solution is prepared containing the following ingredients:

Formulation 5: Aerosol

| Ingredient | Quantity (% by weight) |
|---|---|
| Active ingredient | 0.25 |
| Ethanol | 25.75 |
| Propellant 22 (Chlorodifluoromethane) | 70.00 |

The active ingredient is mixed with ethanol and the mixture added to a portion of the propellant 22, cooled to 30° C., and transferred to a filling device. The required amount is then fed to a stainless steel container and diluted with the remaining propellant. The valve units are then fitted to the container.

Suppositories are prepared as follows:

Formulation 6: Suppositories

| Ingredient | Quantity (mg/suppository) |
|---|---|
| Active ingredient | 250 |
| Saturated fatty acid glycerides | 2,000 |

The active ingredient is passed through a No. 60 mesh U.S. sieve and suspended in the saturated fatty acid glycerides previously melted using the minimal necessary heat. The mixture is then poured into a suppository mold of nominal 2 g capacity and allowed to cool.

An intravenous formulation is prepared as follows:

Formulation 7: Intravenous Solution

| Ingredient | Quantity |
|---|---|
| Active ingredient dissolved in ethanol 1% | 20 mg |
| Intralipid ™ emulsion | 1,000 mL |

The solution of the above ingredients is intravenously administered to a patient at a rate of about 1 mL per minute.

Soft gelatin capsules are prepared using the following:

Formulation 8: Soft Gelatin Capsule with Oil Formulation

| Ingredient | Quantity (mg/capsule) |
|---|---|
| Active ingredient | 10–500 |
| Olive Oil or Miglyol ™ Oil | 500–1000 |

The active ingredient above may also be a combination of therapeutic agents.

GENERAL EXPERIMENTAL PROCEDURES

NMR spectra were recorded on a Varian XL-300 (Varian Co., Palo Alto, Calif.), a Bruker AM-300 spectrometer (Bruker Co., Billerica, Mass.) or a Varian Unity 400 at ambient temperature. Chemical shifts are expressed in parts per million (δ) relative to residual solvent as an internal reference. The peak shapes are denoted as follows: s, singlet; d, doublet; dd, doublet of doublets, t, triplet, q, quartet; m, multiplet; brs=broad singlet; 2s, two singlets. Atmospheric pressure chemical ionization (APCI) mass spectra in alternating positive and negative ion mode were obtained on a Fisons Platform II Spectrometer, Fisons Instruments Manchester U.K.). Chemical ionization mass spectra were obtained on a Hewlett-Packard 5989 instrument (Hewlett-Packard Co., Palo Alto, Calif.) (ammonia ionization, PBMS). Where the intensity of chlorine or bromine-containing ions are described, the expected intensity ratio was observed (approximately 3:1 for $^{35}Cl/^{37}Cl$-containing ions and 1:1 for $^{79}Br/^{81}Br$-containing ions) and the intensity of only the lower mass ion is given. Optical rotations were determined on a Perkin-Elmer 241 polarimeter (Perkin-Elmer Instruments, Norwalk, Conn.) using the sodium D line (λ=589 nm) at the indicated temperature and are reported as follows $[α]_D^{temp}$, concentration (c=g/100 mL), and solvent.

Column chromatography was performed with either Baker Silica Gel (40 μm) (J.T. Baker, Phillipsburg, N.J.) or Silica Gel 50 (EM Sciences, Gibbstown, N.J.) in glass columns or in Flash 40 (Biotage, Dyar Corp. Charlottesville, Va.) columns under low nitrogen pressure. Radial Chromatography was performed using a Chromatron (model 7924T, Harrison Research, Palo Alto, Calif.). Unless otherwise specified, reagents were used as obtained from commercial sources. Dimethylformamide, 2-propanol, tetrahydrofuran, toluene and dichloromethane used as reaction solvents were the anhydrous grade supplied by Aldrich Chemical Company (Milwaukee, Wis.). Microanalyses were performed by Schwarzkopf Microanalytical Laboratory, Woodside, N.Y. The terms "concentrated" and "evaporated" refer to removal of solvent at 5–200 mm of mercury pressure on a rotary evaporator with a bath temperature of less than 45° C. Reactions conducted at "0–20° C." or "0–25° C." were conducted with initial cooling of the vessel in an insulated ice bath which was then allowed to warm to room temperature. The abbreviation "min" and "h" stand for "minutes" and "hours" respectively. The abbreviation "rt" stands for "room temperature." Other abbreviations, which would be readily understandable to one of ordinary skill in the art, are used, such as the following: "$N_2$" stands for nitrogen; "$CH_2Cl_2$" stands for dichloromethane; "THF" stands for tetrahydrofuran; "$NaHCO_3$" stands for sodium bicarbonate.

Preparation 1

2-(Isoquinolin-7-yloxy)-2-methyl-propionic acid ethyl ester

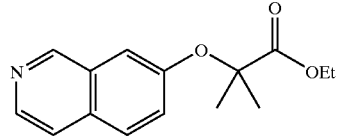

7-Hydroxyisoquinoline (500 mg, 3.4 mmol), ethyl 2-bromoisobutyrate (3 g, 15 mmol) and potassium carbonate (2.1 g, 15 mmol) were mixed in 7 ml of anhydrous DMF. The reaction was heated to 95° C. under $N_2$ for 18 hrs. The reaction was concentrated under reduced pressure and purified by flash column chromatography (33% EtOAc/Hexanes) to yield 470 mg (53%) of the title product of this preparation as a yellow oil.

$^1$H NMR (400 MHz, CDCl$_3$) δ 9.08 (s, 1H), 8.41 (d, 1H), 7.72 (d, 1H), 7.57 (d, 1H), 7.33 (dd, 1H), 7.13 (d, 1H), 4.25 (q, 2H), 1.69 (s, 6H), 1.22 (t, 3H).

Preparation 2

2-(1,2,3,4,4a,8a-Hexahydro-isoquinolin-7-yloxy)-2-methyl-propionic acid ethyl ester

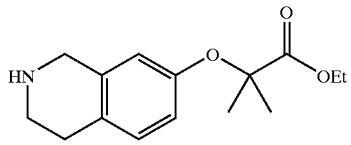

The title product of Preparation 1 (470 mg, 1.8 mmol) and platinum oxide (21 mg, 0.09 mmol) were mixed in 10 ml glacial acetic acid, under 50 psi of $H_2$ at room temperature for 18 hrs. The reaction was filtered though Celite and concentrated under reduced pressure. The residue was diluted with EtOAc and made basic with 1 N NaOH. The organic layer was separated and the aqueous phase was extracted with 3× EtOAc. The organic phases were combined, washed with brine, dried over Na$_2$SO$_4$, filtered and concentrated to yield 443 mg (93%) of the title product of this preparation as a yellow oil.

$^1$H NMR (400 MHz, CDCl$_3$) δ 6.94 (d, 1H), 6.63 (dd, 1H), 6.50 (d, 1H), 4.23 (q, 2H), 3.92 (s, 2H), 3.09 (t, 2H), 2.70 (t, 2H), 1.56 (s, 6H), 1.25 (t, 3H).

Preparation 3

2-Methyl-2-{2-[4-methyl-2-(4-trifluoromethyl-phenyl)-thiazole-5-carbonyl]-1,2,3,4,4a,8a-hexahydro-isoquinolin-7-yloxy}-propionic acid ethyl ester

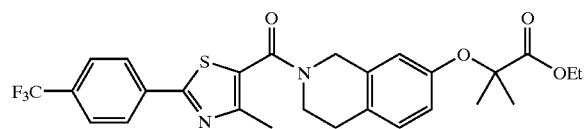

Oxalyl chloride (310 μl, 3.55 mmol) and 5 drops of DMF were added to 4-methyl-2-[4-(trifluoromethyl)phenyl]-5-thiazolecarboxylic acid (1.02 g, 3.55 mmol) (commercially available) in 50 ml of methylene chloride at 0° C. under N$_2$. The reaction was allowed to warm to room temperature and stirred under N$_2$ for 3 hrs. The resulting acid chloride was added dropwise to the title product of Preparation 2 (935 mg, 3.55 mmol) in 50 ml methylene chloride and triethylamine (500 μl, 3.55 mmol) at 0° C. under N$_2$. The reaction was allowed to warm to room temperature and stirred under N$_2$ for 18 hrs. The reaction was diluted with CH$_2$Cl$_2$ and washed with saturated NaHCO$_3$. The organic phase was washed with brine, dried over Na$_2$SO$_4$, filtered and concentrated. The residue was purified by flash column chromatography (33% EtOAc/Hexanes) to yield 1.31 g (70%) of the title product of this preparation.

MS m/z 533 (M+1);
$^1$H NMR (400 MHz, CDCl$_3$) δ 8.05 (d, 2H), 7.71 (d, 2H), 7.03 (d, 1H), 6.70 (dd, 1H), 6.62 (bs, 1H), 4.74 (bs, 2H), 4.23 (q, 2H), 3.81 (bs, 2H), 2.88 (s, 2H), 2.52 (s, 3H), 1.57 (s, 6H), 1.25 (t, 3H).

EXAMPLE 1

2-Methyl-2-{2-[4-methyl-2-(4-trifluoromethyl-phenyl)-thiazole-5-carbonyl]-1,2,3,4-tetrahydro-isoquinolin-7-yloxy}-propionic acid

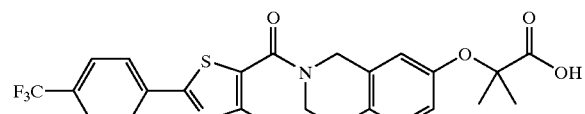

The title product of Preparation 3 (3.12 g, 5.86 mmol) was mixed in 50 ml of 3:1 mixture of EtOH and water. Potassium carbonate (3.24 g, 23.4 mmol) was added and reaction heated to 100° C. for 90 minutes. Reaction was cooled to room temperature and concentrated under reduced pressure. The residue was partitioned between EtOAc and 1 N HCl. The organic phase was washed with water, brine, dried over Na$_2$SO$_4$, filtered and concentrated. The residue was purified by flash column chromatography (1% NH$_4$OH/15% MeOH/CH$_2$Cl$_2$) to yield 2.27 g (77%) of the title product of this example as a white solid.

MS m/z 505 (M+1)
$^1$H NMR (400 MHz, CDCl$_3$) δ 8.04 (d, 2H), 7.70 (d, 2H), 7.08 (d, 1H), 6.81 (dd, 1H), 6.71 (bs, 1H), 4.75 (bs, 2H), 3.84 (bs, 2H), 2.90 (bs, 2H), 2.51 (s, 3H), 1.59 (s, 6H).

Examples 2 to 10 were prepared from analogous starting materials using methods analogous to those described in Example 1:

EXAMPLE 2

2-{2-[2-(4-tert-Butyl-phenyl)-4-methyl-thiazole-5-carbonyl]-1,2,3,4-tetrahydro-isoquinolin-7-yloxy}-2-methyl-propionic acid MS m/z 493 (M+1);
$^1$H NMR (400 MHz CDCl$_3$) δ 7.80 (d, 2H), 7.42 (d, 2H), 6.94 (d, 1H), 6.71 (d, 2H), 6.65 (bs, 1H), 4.66 (bs, 2H), 3.73 (bs, 2H), 2.79 (bs, 2H), 2.43 (s, 3H), 1.45 (s, 6H), 1.32 (s, 9H).

EXAMPLE 3

2-{2-[2-(4-Methoxy-phenyl)-4-methyl-thiazole-5-carbonyl]-1,2,3,4-tetrahydro-isoquinolin-7-yloxy}-2-methyl-propionic acid MS m/z 467 (M+1);
$^1$H NMR (400 MHz CDCl$_3$) δ 7.81 (d, 2H), 6.92 (m, 3H), 6.70 (d 1H), 6.63 (s, 1H), 4.65 (s, 2H), 3.83 (s, 3H), 3.77 (s, 2H), 2.79 (s, 2H), 2.42 (s, 3H), 1.45 (s, 6H).

EXAMPLE 4

2-{2-[2-(3,5-Bis-trifluoromethyl-phenyl)-4-methyl-thiazole-5-carbonyl]-1,2,3,4-tetrahydro-isoquinolin-7-yloxy}-2-methyl-propionic acid MS m/z 573 (M+1);
$^1$H NMR (400 MHz CDCl$_3$) δ 8.34 (s, 2H), 7.93 (s, 1H), 7.03 (d, 1H), 6.77 (d, 1H), 6.67 (bs, 1H), 4.72 (bs, 2H), 3.79 (bs, 2H), 2.87 (bs, 2H), 2.51 (s, 3H), 1.52 (s, 6H).

EXAMPLE 5

2-Methyl-2-{2-[4-methyl-2-(3-trifluoromethyl-phenyl)-thiazole-5-carbonyl]-1,2,3,4-tetrahydro-isoquinolin-7-yloxy}-propionic acid MS m/z 505 (M+1);
$^1$H NMR (400 MHz CDCl$_3$) δ 8.18 (s, 1H), 8.04 (d, 1H), 7.69 (d, 1H), 7.56 (t, 1H), 6.99 (d, 1H), 6.74 (dd, 1H), 6.67 (bs, 1H), 4.70 (bs, 2H), 3.76 (bs, 2H), 2.83 (bs, 2H), 2.47 (s, 3H), 1.49 (s, 6H).

EXAMPLE 6

2-Methyl-2-{2-[4-methyl-2-(2-trifluoromethyl-phenyl)-thiazole-5-carbonyl]-1,2,3,4-tetrahydro-isoquinolin-7-yloxy}-propionic acid $^1$H NMR (400 MHz CDCl$_3$) δ 7.80 (d, 1H), 7.61 (m, 3H), 7.00 (d, 1H), 6.72 (d, 1H), 6.66 (s, 1H), 4.72, (s 2H), 3.77 (s, 2H), 2.86 (s, 2H), 2.49 (s, 3H), 1.47 (s, 6H).

EXAMPLE 7

2-{2-[2-(4-Chloro-phenyl)-4-methyl-thiazole-5-carbonyl]-1,2,3,4-tetrahydro-isoquinolin-7-yloxy}-2-methyl-propionic acid MS m/z 471 (M+1);
$^1$H NMR (400 MHz CDCl$_3$) δ 7.91 (d, 2H), 7.43 (d, 2H), 7.09 (d, 1H), 6.81 (d, 1H), 6.67 (bs, 1H), 4.75 (bs, 2H), 3.85 (bs, 2H), 2.91 (s, 2H), 2.50 (s, 3H), 1.59 (s, 6H).

EXAMPLE 8

2-{2-[2-(3,4-Dimethoxy-phenyl)-4-methyl-thiazole-5-carbonyl]-1,2,3,4-tetrahydro-isoquinolin-7-yloxy}-2-methyl-propionic acid MS m/z 497 (M+1);
$^1$H NMR (400 MHz CD$_3$OD) δ 7.58 (s, 1H), 7.51 (d, 1H), 7.09 (d, 1H), 7.05 (d, 1H), 6.75 (m, 2H), 4.75 (bs, 2H), 3.92 (s, 3H), 3.90 (s, 3H), 3.88 (bs, 2H), 2.91 (bs, 2H), 2.42 (s, 3H), 1.55 (s, 6H).

EXAMPLE 9

2-Methyl-2-{2-[4-methyl-2-(4-trifluoromethoxy-phenyl)-thiazole-5-carbonyl]-1,2,3,4-tetrahydro-isoquinolin-7-yloxy}-propionic acid MS m/z 521 (M+1);
$^1$H NMR (400 MHz CDCl$_3$) δ 7.92 (d, 2H), 7.26 (d, 2H), 6.97 (d, 1H), 6.72 (d, 1H), 6.65 (bs, 1H), 4.68 (bs, 2H), 3.76 (bs, 2H), 2.83 (bs, 2H), 2.45 (s, 3H), 1.46 (s, 6H).

EXAMPLE 10

2-Methyl-2-[2-(4-methyl-2-phenyl-thiazole-5-carbonyl)-1,2,3,4-tetrahydro-isoquinolin-7-yloxy]-propionic acid MS m/z 437 (M+1);
$^1$H NMR (400 MHz CDCl$_3$) δ 7.87 (m, 2H), 7.42 (m 3H), 6.89 (d, 1H), 6.67 (d, 1H), 6.61 (bs, 1H), 4.65 (bs, 2H), 3.70 (bs, 2H), 2.76 (bs, 2H), 2.41 (s, 3H), 1.34 (s, 6H).

Preparation 4

(6-Hydroxy-3,4-dihydro-1H-isoquinolin-2-yl)-[4-methyl-2-(4-trifluoromethyl-phenyl)-thiazol-5-yl]-methanone

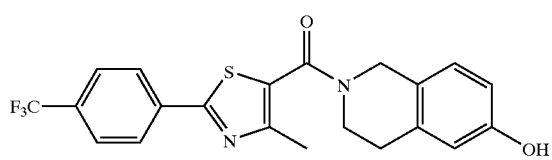

4-Methyl-2-[4-(trifluoromethyl)phenyl]-5-thiazolecarboxylic acid (450 mg, 1.6 mmol), 1-hydroxybenzotriazole (260 mg, 1.9 mmol) and 1-(3-dimethylaminopropyl)-3-ethylcarbodiimide hydrochloride (370 mg, 1.9 mmol) were added to 6-hydroxy-1,2,3,4-tetrahydroisoquinoline hydrobromide (300 mg, 1.3 mmol) in 2 ml of triethylamine and 6 ml of methylene chloride. The reaction was stirred under N$_2$ at RT for 18 hrs. The reaction was diluted with 100 ml CH$_2$Cl$_2$ and made acidic with 10% citric acid. The organic layer was separated and the aqueous phase was extracted with 2×100 ml CH$_2$Cl$_2$. The organic phases were combined, washed with H$_2$O, brine, dried over Na$_2$SO$_4$, filtered and concentrated. The residue was purified by flash column chromatography (40% EtOAc/Hexanes) to yield 229 mg (42%) of the title product of this preparation as a white solid.

$^1$H NMR (400 MHz, CDCl$_3$) δ 8.05 (d, 2H), 7.71 (d, 2H), 6.94(m, 1H), 6.70 (d, 1H), 6.65 (d, 1H), 4.72 (bs, 2H), 3.84 (bs, 2H), 2.90 (s, 2H), 2.52 (s, 3H).

Preparation 5

2-Methyl-2-{2-[4-methyl-2-(4-trifluoromethyl-phenyl)-thiazole-5-carbonyl]-1,2,3,4-tetrahydro-isoquinolin-6-yloxy}-propionic acid ethyl ester

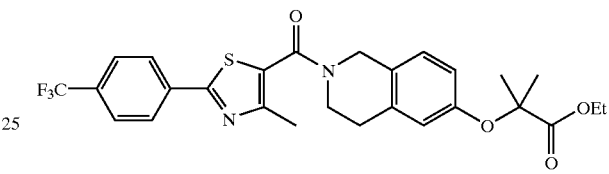

The title product of Preparation 4 (218 mg, 0.52 mmol), ethyl 2-bromoisobutyrate (457 mg, 2.3 mmol) and potassium carbonate (318 mg, 2.3 mmol) were mixed in 2 ml of anhydrous DMF. The reaction was heated to 95° C. under N$_2$ for 18 hrs. The reaction was concentrated under reduced pressure and 50 ml of 1 N HCl was added. The aqueous phase was extracted with EtOAc (3×100 ml). The organic phases were combined, washed with H$_2$O, brine, dried over Na$_2$SO$_4$, filtered and concentrated. The residue was purified by flash column chromatography (25% EtOAc/Hexanes) to yield 194 mg (70%) of the title product of this preparation.

$^1$H NMR (400 MHz, CDCl$_3$) δ 8.05 (d, 2H), 7.71 (d, 2H), 6.99 (bs, 1H), 6.70 (d, 1H), 6.67 (s, 1H), 4.72 (bs, 2H), 4.24 (q, 2H), 3.83 (bs, 2H), 2.89 (s, 2H), 2.51 (s, 3H), 1.59 (s, 6H), 1.28 (t, 3H).

EXAMPLE 11

2-Methyl-2-{2-[4-methyl-2-(4-trifluoromethyl-phenyl)-thiazole-5-carbonyl]-1,2,3,4-tetrahydro-isoquinolin-6-yloxy}-propionic acid

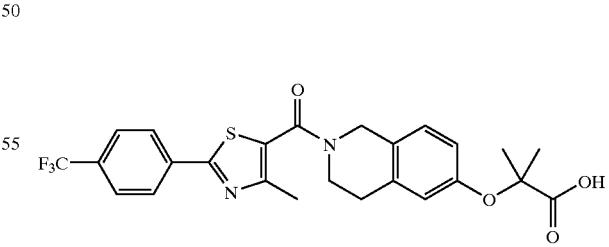

Lithium hydroxide monohydrate (151 mg, 3.6 mmol) in 4 ml of H$_2$O was added to the title product of Preparation 5 (190 mg, 0.36 mmol) in 4 ml of THF. The reaction was stirred at RT for 18 hrs. The reaction was made acidic with 1 N HCl and the THF was removed under reduced pressure. The aqueous phase was extracted with EtOAc (3×50 ml). The organic phases were combined, washed with brine, dried over Na$_2$SO$_4$, filtered and concentrated. The residue was purified by flash column chromatography (1% NH$_4$OH/10% MeOH/CH$_2$Cl$_2$) to yield 113 mg (62%) of the title product of this example as a white solid.

MS m/z 505 (M+1);
$^1$H NMR (400 MHz,CDCl$_3$) δ 8.04 (d, 2H), 7.71(d, 2H), 7.01 (bs, 1H), 6.80 (d, 1H), 6.76 (s, 1H), 4.75 (bs, 2H), 3.84 (bs, 2H), 2.91 (m, 2H), 2.51 (s, 3H), 1.60 (s, 6H).

Examples 12 to 14 were prepared from analogous starting materials using methods analogous to those described in Example 11:

EXAMPLE 12

2-{2-[2-(4-Methoxy-phenyl)-4-methyl-thiazole-5-carbonyl]-1,2,3,4-tetrahydro-isoquinolin-6-yloxy}-2-methyl-propionic acid MS m/z 467 (M+1)
$^1$H NMR (400 MHz CDCl$_3$) δ 7.79 (d, 2H), 6.86 (m, 3H), 6.65 (m, 2H), 4.59 (s, 2H), 3.80 (s, 3H), 3.68 (s, 2H), 2.75 (s, 2H), 2.40(s, 3H), 1.38 (s, 6H).

EXAMPLE 13

2-Methyl-2-{2-[4-methyl-2-(3-trifluoromethyl-phenyl)-thiazole-5-carbonyl]-1,2,3,4-tetrahydro-isoquinolin-6-yloxy}-propionic acid MS m/z 505 (M+1);

$^1$H NMR (400 MHz CDCl$_3$) δ 8.17 (s 1H), 8.03 (d, 1H), 7.68 (d, 1H), 7.55 (t, 1H), 6.90 (bs, 1H), 6.72 (m, 2H), 4.67 (bs, 2H), 3.73 (bs, 2H), 2.81 (s, 2H), 2.47 (s, 3H), 1.46 (s, 6H).

EXAMPLE 14

2-Methyl-2-{2-[4-methyl-2-(2-trifluoromethyl-phenyl)-thiazole-5-carbonyl]-1,2,3,4-tetrahydro-isoquinolin-6-yloxy}-propionic acid MS m/z 505 (M+1);
$^1$H NMR (400 MHz CDCl$_3$) d 7.79 (d, 1H), 7.61 (m, 3H), 6.97 (bs, 1H), 6.76 (m, 2H), 4.71 (bs, 2H), 3.78 (bs, 2H), 2.81 (s, 2H), 2.50 (s, 3H), 1.51 (s, 6H).

What is claimed is:
1. A compound of formula I

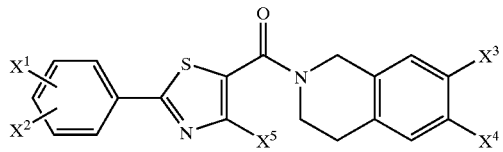

a prodrug of said compound or a pharmaceutically acceptable salt of said compound or prodrug; wherein
X$^1$ and X$^2$ are each independently a) hydrogen, b) halo, c) (C$_1$–C$_4$)alkyl optionally substituted with one to three fluoro or d) (C$_1$–C$_4$)alkoxy optionally substituted with one to three fluoro;
one of X$^3$ and X$^4$ is hydrogen and the other is —Y—C(R$^1$)(R$^2$)—COOH;
Y is —O— or —S—;
R$^1$ and R$^2$ are each independently a) hydrogen or b)(C$_1$–C$_4$)alkyl;
X$^5$ is —CH$_3$ or —CF$_3$.

2. A compound of claim 1 wherein
X$^1$ and X$^2$ are each independently a) hydrogen, b) —CF$_3$, c) —OCF$_3$, d) (C$_1$–C$_4$)alkyl, e) —OCH$_3$ or f) halo;
X$^3$ is —Y—C(R$^1$)(R$^2$)—COOH and X$^4$ is hydrogen;
Y is —O—;
X$^5$ is —CH$_3$.

3. A compound of claim 1 wherein
X$^1$ and X$^2$ are each independently a) hydrogen, b) —CF$_3$, c) —OCF$_3$, d) (C$_1$–C$_4$)alkyl, e) —OCH$_3$ or f) halo;
X$^3$ is hydrogen and X$^4$ is —Y—C(R$^1$)(R$^2$)—COOH;
Y is —O—;
X$^5$ is —CH$_3$.

4. A compound selected from the group consisting of:
2-Methyl-2-{2-[4-methyl-2-(4-trifluoromethyl-phenyl)-thiazole-5-carbonyl]-1,2,3,4-tetrahydro-isoquinolin-7-yloxy}-propionic acid;
2-{2-[2-(4-tert-Butyl-phenyl)-4-methyl-thiazole-5-carbonyl]-1,2,3,4-tetrahydro-isoquinolin-7-yloxy}-2-methyl-propionic acid;
2-{2-[2-(4Methoxy-phenyl)-4-meethyl-thiazole-5-carbonyl]-1,2,3,4-tetrahydro-isoquinolin-7-yloxy}-2-methyl-propionic acid;
2-{2-[2-(3,5-Bis-trifluoromethyl-phenyl)-4-methyl-thiazole-5-carbonyl]-1,2,3,4-tethydro-isoquinolin-7-yloxy}-2-methyl-propionic acid;
2-Methyl-2-{2-[4-methyl-2-(3-trifluoromethyl-phenyl)-thiazole-carbonyl]-1,2,3,4-tetrahydro-isoquinolin-7-yloxy}-propionic acid:
2-Methyl-2-{2-[4-methyl-2-(2-trifluoromethyl-phenyl)-thiazole-5-carbonyl]-1,2,3,4-tetrahydro-isoquinolin-7-yloxy}-propionic acid;
2-{2-[2-(4-Chloro-phenyl)-4-methyl-thiazole-5-carbonyl]-1,2,3,4-tetrahydro-isoquinolin-7-yloxy}-2-methyl-propionic acid;
2-{2-[2-(3,4-Dimethoxy-phenyl)-4-methyl-thiazole-carbonyl]-1,2,3,4-tetrahydro-isoquinolin-7-yloxy}-2-methyl-propionic acid;
2-Methyl-2-{2-[4-methyl-2-(4-trifluoromethoxy-phenyl)-thiazole-5-carbonyl]-1,2,3,4-tetrahydro-isoquinolin-7-yloxy}propionic acid; and
2-Methyl-2{-2-[4-methyl-2-phenyl-thiazole-5-carbonyl}1,2,3,4-tetrahydro-isoquinolin-7-yloxy]-propionic acid;
or a prodrug of said compound or a pharmaceutically acceptable salt of said compound or prodrug.

5. A compound selected from the group consisting of:
2-Methyl-2-{2-[4-methyl-2-(4-trifluoromethyl-phenyl-thiazole-5-carbonyl]1,2,3,4-tetrahydro-isoquinolin-6-yloxy}propionic acid;
2-{2-[2-(4-Methoxy-phenyl)-4-methyl-thiazole-5-carbonyl]-1,2,3,4-tetrahydro-isoquinolin-6-yloxy}-2-methyl-propionic acid;
2-Methyl-2-{2-[4-methyl-2-(3-trifluoromethyl-phenyl)-thiazole-5-carbonyl]-1,2,3,4-tetrahydro-isoquinolin-6-yloxy}-propionic acid; and
2-Methyl-2-{2-[4-methyl-2-(2-trifluoromethyl-phenyl)-thiazole-5-carbonyl]-1,2,3,4-tetrahydro-isoquinolin-6-yloxy}-propionic acid;
or a prodrug of said compound or a pharmaceutically acceptable salt of said compound or prodrug.

6. A pharmaceutical composition which comprises a therapeutically effective amount of a compound of any of claims 1 to 5, a prodrug thereof, or a pharmaceutically acceptable salt of said compound or of said prodrug and a pharmaceutically acceptable carrier, vehicle or diluent.

* * * * *